United States Patent
Liotta et al.

[11] Patent Number: 6,153,596
[45] Date of Patent: Nov. 28, 2000

[54] POLYCATIONIC OLIGOMERS

[75] Inventors: Dennis C. Liotta, McDonough; John A. Petros, Norcross, both of Ga.; Shiow-Jyi Wey, Woburn, Mass.; Joan F. Karr, Decatur; Jan Pohl, Doraville, both of Ga.

[73] Assignee: Emory University, Atlanta, Ga.

[21] Appl. No.: 08/993,008

[22] Filed: Dec. 18, 1997

Related U.S. Application Data

[60] Provisional application No. 60/032,436, Dec. 18, 1996.

[51] Int. Cl.$^7$ .................................. A01N 43/04
[52] U.S. Cl. .......................... 514/44; 435/6; 435/91.1; 435/91.3; 435/69.1; 514/1; 536/22.1; 536/23.1; 536/24.5
[58] Field of Search ................ 435/6, 91.1, 91.3, 435/69.1; 514/1, 44; 536/22.1, 23.1, 24.5

[56] References Cited

U.S. PATENT DOCUMENTS 5,354,844  10/1994  Beug et al. ....................... 530/345

FOREIGN PATENT DOCUMENTS

| | | | |
|---|---|---|---|
| WO91/17773 | 11/1991 | WIPO | A61K 47/48 |
| WO91/19735 | 12/1991 | WIPO | C07K 7/02 |
| WO92/10590 | 6/1992 | WIPO | C12Q 1/68 |
| WO93/07283 | 4/1993 | WIPO | C12N 15/87 |
| WO94/05268 | 3/1994 | WIPO | A61K 31/00 |

OTHER PUBLICATIONS

Akiyama, T. et al. (1986), "The product of the human c–erbB–2 gene: A 185–kilodalton glycoprotein with tyrosine kinase activity," Science 232:1644–1646.

Ausubel, F.M. et al. (eds.), (1996), in *Current Protocols in Molecular Biology*, John Wiley and Sons, Inc., pp. 12.2.1–12.2.10.

Azorin, F. et al. (1985), "Interaction of DNA with Lysine–rich Polypeptides and Proteins. The Influence of Polypeptide Composition and Secondary Structure," J. Mol. Biol. 185:371–387.

Barbier, B. et al. (1984) "Synthesis and β–Conformation of Sequential Polypeptides Containing Arginine, HIstidine, and Leucine," Biopolymers 23:2299–2310.

Barbier, B. and Brack, A. (1988), "Basic Polypeptides Accelerate the Hydrolysis of Ribonucleic Acids," J. Am. Chem. Soc. 110:6880–6882.

Barbier, B. and Brack, A. (1992), "Conformation–Controlled Hydrolysis of Polyribonucleotides by Sequential Basic Polypeptides," J. A. Chem. Soc. 114:3511–3515.

Barrera, D.A. et al. (1995), "Copolymerization and Degradation of Poly–(lactic acid–co–lysine)," Macromolecules 28:425–432.

Barrera, D.A. et al. (1993), "Synthesis and RGD Peptide Modification of a New Biodegradable Copolymer: Poly(lactic acid–co–lysine," J. Am. Chem. Soc. 115:11010–11011.

(List continued on next page.)

*Primary Examiner*—Jezia Riley
*Attorney, Agent, or Firm*—Greenlee, Winner and Sullivan, P.C.

[57] ABSTRACT

The present invention relates to improved methods for introducing nucleic acid into cells by first complexing the nucleic acid with a selected polycationic oligomer which neutralizes the negative charge of the nucleic acid, and then contacting the cell with the complex facilitating uptake of the nucleic acid into the cells as a complex with the oligomer. The methods are preferably applied to introduction of nucleic acid into eukaryotic cells, and more preferably into human cells. The invention also relates to methods of introducing antisense and triplex-forming oligonucleotides into prostate cancer cells to inhibit expression of proteins associated with (or that promote) malignancy and to inhibit cell growth or proliferation. More particularly, the invention relates to a method for inhibiting the expression of the HER-2/NEU protein in prostate cancer cells and to a method for inhibiting prostate cancer cell growth or proliferation.

38 Claims, 3 Drawing Sheets

OTHER PUBLICATIONS

Beaucage, S.L. (1993), "Oligodeoxyribonucleotides synthesis. Phosphoroamidite approach," Methods Mol. Biol. 20:33–61.

Bertram, J. et al. (1994), "Reduction of erbB2 gene product in mamma carcinoma cell lines by erbB2 mRNA–specific and tyrosine kinase consensus phosphorothioate antisense oligonucleotides," Biochem. Biophys. Res. Commun. 200(1):661–667.

Brack, A. and Caille, A. (1978), "Synthesis and β–Conformation of Copolypeptides with Alternating Hydrophilic and Hydrophobic Residues," Int. J. Pept. Protein Res. 11:128–139.

Brown, J. et al. (1974), "Water–soluble Lysine–containing Polypeptides. I. The Synthesis and Characterization of Several Sequential Lysine–Glycine Polypeptides Including a Preliminary Study of their Interaction with DNA," Can J. Chem. 52:3140–3147.

Chowdhury, N.R. et al. (1993), "Fate of DNA Targeted to the Liver by Asialoglycoprotein Receptor–mediated Endocytosis in Vivo," J. Biol. Chem. 268:11265–11271.

Cohen, R.J. et al. (1995), "Immunohistochemical detection of oncogene proteins and neuroendocrine differentiation in different stages of prostate cancer," Pathology 27:229–232.

Cook, P.D. (1993), "Medicinal Chemistry Strategies for Antisense Research," in *Antisense Research and Applications*, Chapter 9, CRC Press, Inc., Boco Raton, pp. 149–187.

Cooney, M. et al. (1978), "Site–specific oligonucleotide binding represses transcription of the human c–myc gene in vitro," Science 241:456–459.

Cotten, M. et al. (1993), "Receptor–Mediated Transport of DNA into Eukaryotic Cells," Meth. Enzymol. 217:618–644.

Cotten, M. et al. (1990), "Transferrin–polycation–mediated introduction of DNA into human leukemic cells: Stimulation by agents that effect the survival of transfected DNA or modulate transferrin receptor levels," Proc. Natl. Acad. Sci. 87:4033–4037.

Curiel, D.T. et al. (1992), "High–Efficiency Gene Transfer Mediated by Adenovirus Coupled to DNA–Polylysine Complexes," Human Gene Therapy 3:147–154.

Curiel, D.T. et al. (1991), "Adenovirus enhancement of transferrin–polylysine–mediated gene delivery," Proc. Natl. Acad. Sci. USA 88:8850–8854.

Durland, R.H. et al. (1991), "Binding of triple helix forming oligonucleotides to sites in gene promoters," Biochemistry 30:9246–9255.

Ebbinghaus, S.W. et al. (1993), "Triplex Formation Inhibits HER–2/neu Transcription In Vitro," J. Clin. Invest. 92:2433–2439.

Ensoli, B. et al. (1994), "Block of AIDS–Karposi's Sarcoma (KS) Cell Growth, Angiogenesis, and Lesion Formation in Nude Mice by Antisense Oligonucleotide Targeting Basic Fibroblast Growth Factor," J. Clin. Invest. 94:1736–1746.

Erickson, B.W. and Merrifield, R.B. (1976), "Solid–phase Synthesis," in *The Proteins*, H. Neurath and R.L. Hill (eds.), vol 2, 3rd Ed., Academic Press, NY, pp. 255–263.

Fields, G.B. and Noble, R.L. (1990), "Solid phase peptide synthesis utilizing 9–fluorenylmethoxycarbonyl amino acids," Int. J. Pept. Protein Res. 35:161–214.

Gao, L. et al. (1993), "Direct In Vivo Gene Transfer to Airway Epithelium Employing Adenovirus–Polylysine–DNA Complexes," Human Gene Therapy 4:17–24.

Harrison, R.W. et al. (1974), "Evidence for Glucocorticoid Transport Through the Target Cell Membrane," Biochem. Biophys. Res. Comm. 61:1262–1267.

Hélène, C. and Toulmë, J.J. (1990), "Specific Regulation of Gene Expression by Antisense, Sense and Antigene Nucleic Acids," Biochim. Biophys. Acta 1049:99–125.

Horwell, D.C. et al. (1994), "'Peptoid' Design," Drug Design and Discovery 12:63–75.

Kessler, H. (1993), "Peptoids—A New Approach to the Development of Pharmaceuticals," Angew Chem. Int. Ed. Engl. 32(4):543–544.

King, C.R. et al. (1985), "Amplification of a novel v–erb-B–related gene in a human mammary carcinoma," Science 229:974–976.

Kruijtzer, J.A.W and Liskamp, R.M.J. (1995), "Synthesis in Solution of Peptoids using Fmoc–protected N–substituted Glycines," Tet. Lett. 36(38):6969–6972.

Kubota, S. et al. (1983), "Conformation of Sequential and Random Copolypeptides of Lysine and Alanine in Sodium Dodecyl Sulfate Solution," Biopolymers 22:2219–2236.

Kubota, S. et al. (1983), "Conformation of Sequential Polypeptides of ($Lys_i$–$Leu_j$), ($Lys_i$–$Ser_j$), (Lys–Gly) in Sodium Dodecyl Sulfate Solution," Biopolymers 22:2237–2252.

Kuhn, E.J. et al. (1993), "Expression of the c–erbB–2 (HER–2/neu) oncoprotein in human prostatic carcinoma," J. Urol. 150:1427–1433.

Leonetti, C. et al. (1996), "Antitumor effect of c–myc antisense phosphorothioate oligodeoxynucleotides on human melanoma cells in vitro and in mice," J. Natl. Cancer Inst. 88(7):419–429.

Liang, T.J. et al. (1993), "Targeted Trasnfection and Expression of Hepatitis B viral DNA in Human Hepatoma Cells," J. Clin. Invest. 91:1241–1246.

Malón, P. et al. (1988), "Conformational Changes of Basic Sequential Polypeptides Induced by Interaction with Porphyrin Molecules," in *Peptides*, Walter de Gruyter & Co., Berlin, pp. 516–518.

McShan, W.M. et al. (1992), "Inhibition of transcription of HIV–1 in infected human cells by oligodeoxynucleotides designed to form DNA triple helices," J. Biol. Chem. 267:5712–5721.

Mellon, K. et al. (1992,) "p53, c–erbB–2 and the epidermal growth factor receptor in the benign and malignant prostate," J. Urol. 147:496–499.

Michael, S.I. et al. (1993), "Binding–incompetent Adenovirus Facilitates Molecular Conjugate–mediated Gene Transfer by the Receptor–mediated Endocytosis Pathway," J. Biol. Chem. 268(10):6866–6869.

Mirabelli, C.K. et al. (1991), "In vitro and In vivo Pharmacologic Activities of Antisense Oligonucleotides," Anti–Cancer Drug Design 6:647–661.

Mouna, A.M. et al. (1994), "Preparation of N–Boc N–Alkyl Glycines for Peptoid Synthesis," Synthetic Commun. 24(17):2429–2435.

Myers, R.B. et al. (1994), "Expression of $p160^{erbB-3}$ and $p185^{erbB-2}$ in Prostatic Intraepithelial Neoplasia and Prostatic Adenocarcinoma," J. Natl. Cancer Inst. 86(15):1140–1145.

Nesterova, M. and Cho–Chung, Y.S. (1995), "A single–injection protein kinase A–directed–antisense treatment to inhibit tumour growth,"Nature Med. 1(6):528–533.

Pietras, R.J. and Szego, C.M. (1977), "Specific binding sites for oestrogen at the outer surfaces of isolated endometrial cells," Nature 265:69–72.

Porumb, H. et al. (1996), "Temporary ex Vivo Inhibition of the Expression of the Human Oncogene HER2 (NEU) by a Triple Helix–forming Oligonucleotide," Cancer Res. 56:515–522.

Potter, H. et al. (1984), "Enhancer–dependent expression of human k immunoglobulin genes introduced into mouse pre–B lymphocytes by electroporation," Proc. Nat. Acad. Sci. USA 81:7161–7165.

Ross, J.S. et al. (1993), "Contribution of HER–2/neu oncogene expression to tumor grade and DNA content analysis in the prediction of prostatis carcinoma metastasis," Cancer 72(10):3020–3028.

Rubenstein, M. et al. (1996), "Antisense oligonucleotide intralesional therapy for human PC–3 prostate tumors carried in athymic nude mice," J. Surg. Oncol. 62:194–200.

Rubenstein, M. et al. (Apr. 1995 Suppl.), "Antisense oligonucleotide induced growth factor deprivation in PC–3 cells enhances bcl–2 expression," Proc. Am. Urol. Assoc. 153:270A, #166.

Rubenstein, M. et al. (1993), "Histologic evaluation of PC–3 tumors treated with antisense oligonucleotides," Proc. Am. Urol. Assoc. 149(4):475A, #1048.

Sadasivan, R. et al. (1993), "Overexpression of HER–2/Neu May be an Indicator of Poor Prognosis in Prostate Cancer," J. Urology 150:126–131.

Semba, I. et al. (1985), "A v–erbB–related proto–oncogene, c–erbB–2, is distinct from c–erb–1 epidermal growth factor–receptor gene and is amplified in a human salivary gland adenocarcinoma," Proc. Natl. Acad. Sci. 82:6497–6501.

Sensibar, J.A. et al. (1995), "Prevention of death cell induced by tumor necrosis factor $\alpha$ in LNCaP cells by overexpression of sulfated glycoprotein–2 (clusterin)," Cancer Res. 55(11):2431–2437.

Sikes, R.A. and Chung, L.W.K. (1992), "Acquisition of a Tumorigenic Phenotype by a Rat Ventral Prostate Epithelial Cell Line Expressing a Transfected Activated neu Oncogene," Cancer Res. 52:3174–3181.

Simon, R.J. et al. (1994), "Using Peptoid Libraries [Oligo N–Substituted Glycines] for Drug Discovery," in *Techniques Protein Chem V*, Crabb, J.W. (ed.), Academic Press, pp. 533–539.

Skorski, T. et al. (1996), "Antisense Oligodeoxynucleotide Combination Therapy of Primary Chronic Myelogenous Leukemia Blast Crisis in SCID Mice," Blood 88(3):1005–1012.

Skorski, T. et al. (1995), "Leukemia Treatment in Severe Combined Immunodeficiency Mice by Antisense Oligonucleotides Targeting Cooperating Oncogenes," J. Exp. Med. 182:1645–1653.

Steinsipar, J. and Muldoon, T.G. (1991), "Role of microsomal receptors in steroid hormone action," Steroids 56:66–71.

Stull, R.D. and Szoka, F.C., Jr. (1995), "Antigene, Ribozyme and Aptamer Nucleic Acid Drugs: Progress and Prospects," Pharm. Res. 12(4):465–483.

Stull, et al. (1992), "Predicting Antisense Oligonucleotide Inhibitory Efficacy: a computational approach using histograms and thermodynamic indices," Nucl. Acids. Res. 20(13):3501–3508.

Stull, R.A. et al. (1991), "A Protocol for Selection of Antisense Target Sequences," Pharm. Res. (NY) 10 Suppl. S56 (Sixth Annual Meeting Am. Assoc. Pharm. Scientists, Washington, DC, Nov. 17–21, 1996).

Uhlmann, E. and Peyman, A. (1990), "Antisense Oligonucleotides: A New Therapeutic Principle," Chem. Rev. 90:544–584.

Veldscholte, J. et al. (1990), "Unusual specificity of the androgen receptor in the human prostate tumor cell line LNCaP: high affinity for progestagenic and estrogenic steroids," Biochim. Biophys. Acta 1052:187–194.

Veldscholte, J. et al. (1992), "The Androgen Receptor in LNCaP Cells Contains a Mutation in the Ligand Binding Domain which Affects Steroid Binding Characteristics and Response to Antiandrogens," J. Steroid Biochem. Mol. Biol. 41:665–669.

Vives, J. et al. (1985), "Solid–State Conformation of Some Basic Sequential Polypeptides," Biopolymers 24:1801–1808.

Wagner, F. et al. (1990), "Transferrin–polycation conjugates as carriers for DNA uptake into cells," Proc. Natl. Acad. Sci. 87:3410–3414.

Wu, G.Y. and Wu, C.H. (1987), "Receptor–mediated in Vitro Gene Transformation by a Soluble DNA Carrier System," J. Biol. Chem. 262:4429–4432.

Yazaki, T. et al. (1996), "Treatment of glioblastoma U–87 by systemic administration of an antisense protein kinase C–alpha phosphorothioate oligodeoxynucleotide," Mol. Pharm. 50:236–242.

Zenke, M. et al. (1990), "Receptor–mediated endocytosis of transferrin–polycation conjugates: An efficient way to introduce DNA into hematopoietic cells," Proc. Natl. Acad. Sci. USA 87:3655–3659.

Zhau, H.E. et al. (1992), "Expression of c–erbB–2/neu proto–oncogene in human prostatic cancer tissues and cell lines," Mol. Carcin. 5:320–327.

Zhau, H.Y.E. et al. (1996), "Transfected neu Oncogene Induces Human Prostate Cancer Metastasis," The Prostate 28:73–83.

Zhou, X. et al. (1990), "Lipophilic polylysines mediate efficient DNA transfection in mammalian cells," Biochim. Biophys. Acta 1065:8–14.

Zuckermann, R.N. et al. (1994), "Discovery of Nanomolar Ligands for 7–Transmembrane G–Protein–Coupled Receptors from a Diverse N–(Substituted)glycine Peptoid Library," J. Med. Chem. 37:2678–2685.

Zuckermann, R.N. et al. (1992), "Efficient Method for the Preparation of Peptoids [Oligo(N–substituted glycines) by Submonomer Solid–Phase Synthesis," J. Am. Chem. Soc. 114:10646–10647.

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Oligonucleotide"

(iii) HYPOTHETICAL: NO (xi) SEQUENCE DESCRIPTION: SEQ ID NO:1:

GGGAGGAGGA GGTGGAGGAG GAGGAGGA      28

(2) INFORMATION FOR SEQ ID NO:2:

(i) SEQUENCE CHARACTERISTICS:
      (A) LENGTH: 28 base pairs
      (B) TYPE: nucleic acid
      (C) STRANDEDNESS: double
      (D) TOPOLOGY: unknown (ii) MOLECULE TYPE: DNA (genomic)

-continued (iii) HYPOTHETICAL: NO (iv) ANTI-SENSE: NO (xi) SEQUENCE DESCRIPTION: SEQ ID NO:2:

AGGAGAAGGA GGAGGTGGAG GAGGAGGG                                           28

(2) INFORMATION FOR SEQ ID NO:3:

(i) SEQUENCE CHARACTERISTICS:
            (A) LENGTH: 28 base pairs
            (B) TYPE: nucleic acid
            (C) STRANDEDNESS: double
            (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:3:

CCCTCCTCCT CCACCTCCTC CTTCTCCT                                           28

(2) INFORMATION FOR SEQ ID NO:4:

(i) SEQUENCE CHARACTERISTICS:
            (A) LENGTH: 24 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (xi) SEQUENCE DESCRIPTION: SEQ ID NO:4:

Lys Ala Lys Ala Lys Ala Lys Ala Lys Ala Lys Ala Lys Ala Lys Ala
1               5                   10                  15

Lys Ala Lys Ala Lys Ala Lys Ala
            20

(2) INFORMATION FOR SEQ ID NO:5:

(i) SEQUENCE CHARACTERISTICS:
            (A) LENGTH: 48 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (xi) SEQUENCE DESCRIPTION: SEQ ID NO:5:

Lys Ala Lys Ala Lys Ala Lys Ala Lys Ala Lys Ala Lys Ala Lys Ala
1               5                   10                  15

Lys Ala Lys Ala Lys Ala Lys Ala Lys Ala Lys Ala Lys Ala Lys Ala
            20                  25                  30

Lys Ala Lys Ala Lys Ala Lys Ala Lys Ala Lys Ala Lys Ala Lys Ala
                35                  40                  45

(2) INFORMATION FOR SEQ ID NO:6:

```
    (i) SEQUENCE CHARACTERISTICS:
        (A) LENGTH: 56 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (xi) SEQUENCE DESCRIPTION: SEQ ID NO:6:

Lys Ala Lys Ala Lys Ala Lys Ala Lys Ala Lys Ala Lys Ala Lys Ala
1               5                   10                  15

Lys Ala Lys Ala Lys Ala Lys Ala Lys Ala Lys Ala Lys Ala Lys Ala
            20                  25                  30

Lys Ala Lys Ala Lys Ala Lys Ala Lys Ala Lys Ala Lys Ala Lys Ala
        35                  40                  45

Lys Ala Lys Ala Lys Ala Lys Ala
    50                  55
```

POLYCATIONIC OLIGOMERS

This application takes priority under 35 U.S.C.§ 199(e) from U.S. provisional application Ser. No. 60/032,436 filed Dec. 18, 1996 which is incorporated in its entirety by reference herein.

FIELD OF THE INVENTION

This invention relates to polycationic carriers which function as nucleic acid binding agents. The invention includes methods for introduction of the nucleic acid into living cells. The invention also relates to inhibition of prostate cancer cells by introduction of oligonucleotides which inhibit protein expression into cells.

BACKGROUND OF THE INVENTION

Efficient and selective methods for introducing exogenous nucleic acid, including various forms of DNA and RNA, into living cells are important for applications in basic research and in therapeutics. Methods which minimize loss of functionality of the nucleic acid and which are selective for types of mammalian cells are of particular importance. Such methods and the nucleic acid-complexing and cell-targeting reagents used in such methods are important tools in basic research and gene therapy. Methods and reagents for efficient introduction of functional antisense and antigene agents into eukaryotic cells are of particular importance.

A variety of therapeutic methods based on introduction of nucleic acids into cells have been proposed. See, for example, Uhlmann, E. and Peyman, A. (1990) "Antisense Oligonucleotides: A New Therapeutic Principle" *Chemical Reviews* 90:544–584; Hélène, C. and Toulmé, J. J. (1990) "Specific Regulation of Gene Expression by Antisense, Sense and Antigene Nucleic Acids" *Biochim. Biophys. Acta* 1049:99–125; Mirabelli, C. K. et al. (1991) "In Vitro and In Vivo Pharmacologic Activities of Antisense Oligonucleotides" *Anti-Cancer Drug Design* 6:647–661; Cook, P. D. (1993) "Medicinal Chemistry Strategies for Antisense Research" In Crooke, S. T. and Lebleu, B. (eds.) *Antisense Research and Applications,* CRC Press, Boca Raton, pages 147–189; and Stull, R. A. and Szoka, F. C. Jr. (1995) "Antigene, Ribozyme and Aptamer Nucleic Acid Drugs: Progress and Prospects" *Pharmaceutical Research* 12(4) :465–483.

The introduction of expressible DNA (deoxyribonucleic acids) or RNA (ribonucleic acids) into cells can result in expression of therapeutic peptides to correct genetic defects or inhibit disease conditions. For example, introduction and expression of tumor suppressor genes or metastasis suppressor genes is proposed for cancer therapy. Nucleic acids can also enhance or inhibit gene expression in cells. For example, antisense agents, which target messenger RNA, and antigene agents, which bind to double-stranded DNA, can inhibit undesirable or harmful expression of genes or inhibit viral infection or proliferation. See, for example, WO 92/10590 "Inhibition of Transcription by Formation of Triple Helixes" (Toole et al.) published Jun. 25, 1992. See also, for example, Stull, R. A. et al. (1992) "Predicting Antisense Oligonucleotide Inhibitory Efficacy" *Nucleic Acids Res.* 20(13):3501–3508; Stull, R. A. et al. (1991), "A Protocol for Selection of Antisense Target Sequences," *Pharm. Res.* (*NY*) 10 Suppl. S56 (Sixth Annual Meeting Am. Ass. Pharm. Scientists Washington, D.C., Nov. 17–21, 1996.)

This invention relates, in part, to inhibition of prostate cancer cells by introduction of triplex-forming oligonucleotides into the cells.

Triplex forming oligonucleotides have recently been developed for therapeutic applications (see, for example, PCT application WO 94/05268). Triplex formation is a site-specific phenomenon in which a single-stranded oligonucleotide forms specific G:G-C and A:A-T bonds, by Hoogsteen hydrogen bonding, with a target site in a gene promoter, thereby preventing the binding of nuclear proteins to the promoter. Preferred triplex target sequences are polypurine-polypyrimidine regions within promoter regions of genes, such as oncogenes or proto-oncogenes, the expression of which promote malignancy.

Antisense and triplex-forming oligonucleotides have been evaluated in several tumor models and in viral-infected cells for therapeutic applications. See: Skorski, T. et al. (1996), "Antisense oligodeoxynucleotide combination therapy of primary chronic myelogenous leukemia blast crisis in SCID mice," *Blood* 88(3):1005–1012); Ensoli, B. et al. (1994), "Block of AIDS-Kaposi's sarcoma (KS) cell growth, angiogenesis, and lesion formation in nude mice by antisense oligonucleotide targeting basis fibroblast growth factor," *J. Clin. Invest.* 94:1736–1746; Skorski, T. et al. (1995), "Leukemia treatment in severe combined immunodeficiency mice by antisense oligonucleotides targeting cooperating oncogenes," *J. Exp. Med.* 182:1645–1653; Leonetti, C. et al. (1996), "Antitumor effect of c-myc antisense phosphorothioate oligodeoxynucleotides on human melanoma cells in vitro and in mice," *JNCI* 88(7) :419–429; Yazaki, T. et al. (1996), "Treatment of glioblastoma U-87 by systemic administration of an antisense protein kinase C-alpha phosphorothioate oligodeoxynucleotide," *Mol. Pharm.* 50:236–242; Nesterova, M. and Cho-Chung, Y. S. (1995), "A single-injection protein kinase A-directed antisense treatment to inhibit tumour growth," *Nature Med.* 1(6):528–533; Cooney, M. et al. (1988) "Site-specific oligonucleotide binding represses transcription of the human c-myc gene in vitro," *Science* (*Wash. D.C.*) 241:456–459; Durland, R. H. et al. (1991) "Binding of triple helix forming oligonucleotides to sites in gene promoters," *Biochemistry* 30:9246–9255; McShan, W. M. et al. (1992) "Inhibition of transcription of HIV-1 in infected human cells by oligodeoxynucleotides designed to form DNA triple helices," J. Biol. Chem 267:5712–5721.

Some literature reports relate to the use of antisense oligonucleotides for treating prostate cancer. Transfection of the LNCaP prostate cancer cell line with a 21 base ligonucleotide antisense to sulfated glycoprotein-2 (SGP-2) was reported to decrease SGP-2 biosynthesis and increase cell death (Sensibar, J. A. et al. (1995), "Prevention of cell death induced by tumor necrosis factor alpha in LNCaP cells by overexpression of sulfated glycoprotein-2 (clusterin)," *Cancer Res.* 55(11):2431–2437). However, a variable response in nude mice growing subcutaneous xenografts of the prostate cancer PC-3 cell line (ranging from no effect to a single complete response) was reported from intralesional injection of antisense oligonucleotides directed against transforming growth factor-alpha (TGF-alpha) and epidermal growth factor receptor (EGFR)(Rubenstein, M. et al. (1996), "Antisense oligonucleotide intralesional therapy for human PC-3 prostate tumors carried in athymic nude mice," *J. Surg. Oncol.* 62:194–200; Rubenstein, M. et al. (1995), "Antisense oligonucleotide induced growth factor deprivation in PC-3 cells enhances bcl-2 expression," *J. Urol.* 153(4) :270A; Rubenstein, M. (1993), "Histologic evaluation of PC-3 tumors treated with antisense oligonucleotides," *J. Urol.* 149(4):475A).

The human her-2/neu proto-oncogene also known as c-erbB-2, erbB-2, neu, and her-2 identified in human tumor tissue is homologous to the epidermal growth factor receptor, and possesses an intracellular domain with tyrosine specific kinase activity and an extracellular domain (Sumba, K. et al. (1985), "A v-erbB-related proto-oncogene, c-erbB-2, is distinct from the c-erb-1 epidermal growth factor-receptor gene and is amplified in a human salivary gland adenocarcinoma," *Proc. Natl. Acad. Sci.* 82:6497; King, C. R. et al. (1985), "Amplification of a novel v-erbB-related gene in a human mammary carcinoma," *Science* 229:974; Akiyama, T. et al. (1986), "The product of the human c-erbB-2 gene: A 185-kilodalton glycoprotein with tyrosine kinase activity," *Science* 232:1644–1646).

Overexpression of the HER-2/NEU protein has been documented in many human malignancies, including breast, ovary, colon, salivary gland, stomach, lung, kidney, bladder, and endometrium; however, the greatest proportion of cases that express HER-2/NEU may be in prostate cancer cells (Myers, R. B. et al. (1994), "Expression of p160$^{erbB-3}$ and p185$^{erbB-2}$ in prostatic intraepithelial neoplasia and prostatic adenocarcinoma," *JNCI* 86(15): 1140–1145). Recent studies report that 16% to 80% of prostate cancers overexpress HER-2/NEU at the protein level (Mellon, K. et al. (1992), "p53, c-erbB-2, and the epidermal growth factor receptor in the benign and malignant prostate," *J. Urol.* 147:496–499; Zhau, H. E. et al. (1992), "Expression of c-erb B-2/neu proto-oncogene in human prostatic cancer tissues and cell lines," *Mol. Carcin.* 5:320–327; Ross, J. S. et al. (1993), "Contribution of her-2/neu oncogene expression to tumor grade and DNA content analysis in the prediction of prostatic carcinoma metastasis," *Cancer* 72(10):3020–3028;Kuhn, E. J. et al. (1993), "Expression of the c-erbB-2 (her-2/neu) oncoprotein in human prostatic carcinoma," *J. Urol.* 150:1427–1433; Cohen, R. J. et al. (1995), "Immunohistochemical detection of oncogene proteins and neuroendocrine differentiation in different stages of prostate cancer," *Pathology* 27:229–232).

Experimental transfection of an activated neu oncogene into a non-tumorigenic rat prostate epithelial cell line resulted in acquisition of a tumorigenic phenotype (Sikes, R. A. and Chung, L. W. K. (1992), "Acquisition of a tumorigenic phenotype by a rat ventral prostate epithelial line expressing a transfected activated neu oncogene," *Cancer Res.* 52:3174–3181). When human prostate cancer cell line PC-3 was similarly transfected, those clones with high copy number showed greatly enhanced metastatic capacity (Zhau, H. Y. E. et al. (1996), "Transfected neu oncogene induces human prostate cancer metastasis," *The Prostate* 28:73–83). These studies show that her-2/neu can act as a single step transforming agent in benign cells, and that increased expression leads to a more aggressive phenotype in human prostate cancer cells.

The her-2/neu gene is a potential target for oligonucleotide therapy in prostate cancer. Inhibition of translation of the mRNA corresponding to the her-2/neu gene by antisense oligonucleotides in cellular systems has been reported (Bertram, J. et al. (1994), "Reduction of erbB2 gene product in mammary carcinoma cell lines by erbB2 mRNA-specific and tyrosine kinase consensus phosphorothioate antisense oligonucleotides," Biochem. Biophys. Res. Commun. 200:661–667).

A purine-rich (G and A) region of the her-2/neu promoter has been identified as a potential target for inhibition by triplex-forming oligonucleotides (Ebbinghaus S. W. et al. (1993) "Triplex formation inhibits HER-2/neu transcription in vitro," J. Clin. Invest. 92:2433–2439). An oligodeoxyribonucleotide designated HN28ap (human neu 28-mer antiparallel, i.e., reversed in orientation with respect to the genomic target) and having the sequence:

5'-G GGA GGA GGA GGT GGA GGA GGA GGA GGA-3' (SEQ ID NO:1)

was reported to form triplexes with the target site in vitro, while the corresponding parallel oligonucleotide did not. In an in vitro run-off transcription assay her-2/neu transcription was reported to be inhibited by HN28ap in a concentration dependent fashion with substantial inhibition seen at 2.5 $\mu$M and complete inhibition at an oligonucleotide concentration of 25 $\mu$M.

There appear to be no reports of the effect of HN28ap on her-2/neu message or protein levels in prostate cancer cells either in vitro or in vivo. However, a 28 base oligonucleotide differing from HN28ap by one base (T→C) at position 13, was shown to inhibit her-2/neu transcription/translation in the breast cancer cell line MCF7 (Porumb, H. et al. (1996), "Temporary ex vivo inhibition of the expression of the human oncogene HER2 (NEU) by a triple helix-forming oligonucleotide," Cancer Res. 56:515–522). In this case, liposome-mediated transfection was used to introduce the oligonucleotide, free oligonucleotide was not effective, and the effect observed was transient. There has been no definitive demonstration of the effectiveness of oligonucleotide therapy in prostate cancer.

High efficiency introduction of the nucleic acid into living cells is an important aspect of the development of any effective nucleic acid therapeutic. In addition introduction of the nucleic acid therapeutic in to a particular type of cell can be important. For example, specific cell targeting of such therapeutics is critical in cancer therapy directed toward killing cancerous or metastatic cells in order to maximize target cell death and minimize damage to healthy cells. Furthermore, cell targeting of the nucleic acid can result in higher concentrations at the target site and improved therapeutic efficiency.

Several methods that are reported to provide high efficiency introduction of nucleic acids into living cells employ polycations as components of cell transfection compositions. For example, receptor-mediated endocytosis employing polycationic nucleic binding agents covalently linked to ligands of cell surface receptors has resulted in cell-selective, high-efficiency transfection.

Polylysine in its polycationic form binds to polynucleic acids, such as DNA, to form soluble complexes. Polylysine has been employed as a component of compositions for introduction of DNA into cells. Conjugates of polylysine and N-glutaryl-phosphatidylethanolamine (NGPE) effect DNA transfection of cultured cells. These conjugates, carrying an average of 2 NGPEs per polymer, have been designated "lipopolylysine" (Zhou, X. et al. (1991) *Biochim. Biophysica Acta* 1065:8–14). Lipopolylysine-DNA complexes are believed to bind to cell surfaces and to be internalized into cells via endosomes or lysosomes.

Polylysine covalently linked to a cell receptor specific ligand has been employed to complex DNA and facilitate its entry into cells via receptor-mediated endocytosis. See Cotten, M. et al. (1993) *Methods in Enzymol.* 217:618–644 for a review of methods relying on receptor-mediated endocytosis. For example, polylysine conjugates with the iron transport protein transferrin are reported to provide highly efficient nucleic acid delivery into certain cells (Wagner, F. et al. (1990) *Biochemistry* 87:3410–3414; Cotten, M. et al. (1990) *Biochemistry* 87:4033–4037; and Zenke, M. et al. (1990) *Proc. Natl. Acad. Sci. USA* 87:3655–3659).

Liver cells (hepatocytes and hepatoma cells, for example) express specific surface receptors for asialoglycoproteins, such as asialoorosomucoid. A soluble DNA carrier and targeting system consisting of an asialoglycoprotein linked to polylysine has been used to bind DNA and hepatitis B virus DNA constructs to liver cells and to effect DNA delivery into targeted cells. Asialoorosomucoid covalently linked to polylysine and complexed to DNA creates a soluble DNA delivery system targeted for cells expressing the asialoglycoprotein receptor. The system has been demonstrated to be receptor-mediated and selective for cells which express the asialoglycoprotein receptor (Wu, G. Y. and Wu, C. H. (1987) *J. Biol. Chem.* 262:4429–4432; Liang, T. J. et al. (1993) *J. Clin. Invest.* 91:1241–1246; and Chowdhury, N. R. et al. (1993) *J. Biol. Chem.* 268:11265–11271).

PCT application WO 91/17773, published Nov. 28, 1991, relates to a system for transporting nucleic acids which displays specificity for T-cells. This system employs proteins capable of binding to cell surface receptors expressed on T-cells, for example proteins capable of binding to CD4, the receptor used by the HIV virus. A polycation conjugate with a CD4-binding protein is complexed with DNA and the resulting complex used to transfer the DNA into T-cells.

A problem with receptor-mediated endocytosis has been the destruction of the nucleic acid by lysosomal action during endocytosis. Addition of replication-deficient adenovirus during transfection via receptor-mediated endocytosis has been reported to enhance delivery of functional DNA into cells. Polylysine-DNA complexes coupled to adenovirus are reported to result in efficient transfer of DNA into cells having adenovirus receptors. Ternary complexes composed of polylysine-adenovirus conjugates and polylysine-transferrin conjugates and DNA are also reported to give efficient DNA delivery (Curiel, D. T. et al. (1992) *Human Gene Therapy* 3:147–154; Curiel. D. T. et al. (1991) *Proc. Natl. Acad. Sci. USA* 88:8850–8854; PCT application PCT/EP92/02234, claiming priority to U.S. patent application Ser. No. 07/937,788 filed Sep. 2, 1992; Gao, L. et al. (1993) *Human Gene Therapy* 4:17–24; and Michell, S. L. et al. (1993) *J. Biol. Chem.* 268:6866–6869).

Steroid hormones interact with components of biological membranes and may enter their respective target cells by diffusion or by a membrane-mediated process which is saturable and temperature-dependent (Pietras, R. J. and Szego, C. M. (1977) *Nature* 265:69–72). Plasma membranes of target cells may contain steroid receptors (Steinsapir, J. and Muldoon, T. G. (1991) *Steroids* 56:66–71). The human androgen receptor (See; Coffey, O. S. (1992) In *Campbell's Urology*, 6th Edition, Walsh, P. C. et al. (eds.), W. B. Saunders Co., Philadelphia, Pa.) can be found in prostate tissue, metastatic prostate cancer tissue, hair follicles, muscle and skin; it can be cytoplasmic but can also be located in cell membranes. A specific mechanism, associated with the cell membrane, must transport steroids into the target cell before they can bind to the cytosolic receptor (Harrison, R. W. et al. (1974) *Biochem. Biophys. Res. Comm.* 61:1262–1267).

Androgen receptors have affinity for a number of androgens and other steroids. Prostate tumor cells have affinity for progestagenic and estrogenic steroids and antiandrogens, such as cyproterone (Veldscholte, J. et al. (1990) *Biochim. Biophys. Acta.* 1052:187–194; and Veldscholte, J. et al. (1992) *J. Steroid Biochem. Mol. Biol.* 41:665–669).

Pending U.S. patent application Ser. No. 08/283,238, of Petros and Liotta filed Jul. 29, 1994, which is incorporated in its entirely by reference herein, provides a water-soluble system for nucleic acid delivery to cells having androgen receptors. A steroid moiety capable of binding to an androgen receptor is covalently linked to a polycation, such as polylysine, polyarginine, polyhistidine or protamine. The polycation-steroid conjugate is complexed with a single-stranded nucleic acid, such as a single-stranded DNA molecule, and contacted with target cells to effect transfection of the cells with the nucleic acid. Polycations that bind nucleic acids which are targeted to specific cells by covalent linkage to ligands of cell surface receptors can be used to detect the presence and location of cells which express that receptor. The polycation can be labelled for detection by complexation to radiolabelled nucleic acid, for example.

This invention relates, in part, to the use of polycationic oligomers to bind and effect charge neutralization of oligonucleotides. Polycationic oligomers of this invention include certain sequential (or alternating) oligomers with cationic groups, such as lysine (Lys) or arginine (Arg), alternating with non-cationic groups along the oligomer chain. Sequential polycationic oligomers of this invention include polypeptides, e.g. $(Lys-AAA)_n$, where AAA is an amino acid with a non-cationic side group and n is the number of repeating units in the oligomer, oligomers having alternating cationic amino acids and lactate residues, e.g. the sequential copolymer $[Lys-Lac]_n$, and peptoids with alternating cationic groups.

Conformational studies of sequential peptides and DNA complexes with certain sequential peptides have been reported (Kubota, S. et al. (1983) *Biopolymers* 23:2219–2236 (1) and Kubota S. et al. (1983) *Biopolymers* 23:2237–2252 (2)). These references report the investigation of the conformation of several sequential polypeptides in surfactant solution including $[Lys-Ala]_n$ (n>54); $[Lys-Leu]_n$ (n>28); $[Lys-Ser]_n$ (n>30); and $[Lys-Gly]_n$ (n>34). Methods of synthesis of the listed sequential polypeptides were also reported.

Vives, J. et al (1985) *Biopolymers* 24:1801–1808 report X-ray diffraction studies of the structure of solid films of several alternating polypeptides including poly(Ala-Lys), poly(Leu-Lys), poly(Val-Lys), and poly(Arg-Leu). The size of these polypeptides was estimated to range from 25–80 amino acid residues. The authors refer to Brach, A. and Caille, A. (1978) *Int. J. Pept. Protein Res.* 11:128–139 and Barbier, B. et al. (1984) *Biopolymers* 23:2299–2310 for methods of synthesis. Malon, P. et al. (1988) *Peptides* pgs. 516–518 report studies of conformational changes induced by interaction with porphyrin in basic sequential polypeptides including $(Lys-Ala)_n$ (MWt. range 6,500 to 10,000). Azorin, F. et al. (1985) *J. Mol. Biol.* 185:371–387 reports X-ray diffraction studies of fibers of DNA complexes with several sequential polypeptides including poly(Leu-Lys), poly(Val-Lys), and poly(Ala-Lys). The authors refer to Brach and Caille (1978) supra and Vives et al. (1985) supra for methods of synthesis of sequential polypeptides.

Barbier, B. and Brach, A. (1988) *J. Amer. Chem. Soc.* 110:6880–6882 and Barbier, B. and Brach, A. (1992) *J. Amer. Chem. Soc.* 114:3511–3515 report that certain sequential basic polypeptides can accelerate hydrolysis of oligoribonucleotides under basic conditions (pH 8). Poly(Leu-Lys), poly(Arg-Leu) and poly(Ala-Lys) were reported to hydrolyze 85%, 68% and 33%, respectively, of the phosphodiester bonds of oligo(A)'s over 7 days (at 50° C.) compared to 27% hydrolysis by polylysine under similar conditions. The authors explain the enhanced hydrolytic activity of these basic polypeptides as a result of the spatial geometry of the peptide backbone in a β-sheet conformation and the regular spacing of charged residues (6.9Å) in the sequential peptide comparable to the spacing (6.2Å) between consecutive phosphate groups in the oligoribonucleotide.

Poly(lactic acid) is a biodegradable polymer widely used as a biomedical material. The random copolymer, poly(lactic acid-co-lysine), has been prepared and suggested as an alternative to poly(lactic acid) in biomedical applications, particularly as a matrix material for tissue engineering. See: D. A. Barrera et al. (1993) J. Am. Chem. Soc. 115:11010–11011 and D. A. Barrera et al. (1995) Macromolecules 28:425–432. Incorporation of lysine residues into poly(lactic acid) provides chemically reactive sites for derivatizing the material to alter its surface with biologically active moieties. The first copolymer prepared was reported to have an average molecular weight of 64,000 g/mol and to contain 1.3 mol % lysine. Copolymers ranging in molecular weight from about 7,000 to 95,000 and lysine mol % from 2.4 to 6.4 were also reported. Materials with properties desirable for biomedical applications are reported to contain 1–10 mol % lysine. Higher concentrations of lysine in the co-polymer are said to alter the physical characteristics of the polymer poly(lactic acid) and to be deleterious to degradability. It was also reported that the copolymer was derivatized via its lysine residues with a cell adhesion promoting peptide.

Peptoids, i.e., N-substituted oligoglycines, have recently been considered for the development of pharmaceuticals. H. Kessler (1993) Angew. Chem. Int. Ed. Engl. 32(4):543–544. Peptoid libraries, prepared by combinatorial synthesis and containing large numbers of structurally different peptoids, have been screened for peptoids having biological function. Such libraries have, for example, been screened for peptoids with affinity for binding to ligands (J. A. W. Kruijtzer and R. M. J. Liskamp 91995) Tet. Letts. 36(38):6969–6972; R. N. Zuckermann et al. (1994) J. Med. Chem. 37:2678–2685; R. J. Simon et al. (1994) Techniques Protein Chem. V (Academic Press) pp:533–539). A strategy for rational design of peptoids that bind as ligands to proteins has been described (D. C. Howell et al. (1994) Drug Design and Discovery 12:63–75). WO91/19735 (P. A. Bartlett et al.) published Dec. 26, 1991, describes a method for generating and screening peptoid libraries to isolate peptoids with selected biological functions. This published application, which is incorporated in its entirety by reference herein, also describes or refers to literature methods for the synthesis of peptoids, for example by solid phase synthesis, and describes sources of N-substituted glycine analogues as starting materials for peptoid synthesis. The application specifically describes screening of peptoid libraries for peptoids that bind to protein or peptide receptors. Conjugates of selected peptoids to pharmaceutically active compounds, in particular peptoid-trimethoprim conjugates, are disclosed. The application notes that steroid conjugates of peptoids can also be made.

SUMMARY OF THE INVENTION

The present invention relates to improved methods for introducing nucleic acid into cells by first complexing the nucleic acid with a size-selected polycationic oligomer which neutralizes the negative charge of the nucleic acid, and then contacting the cell with the complex facilitating uptake of the nucleic acid into the cells as a complex with the oligomer. The methods are preferably applied to introduction of nucleic acid into eukaryotic cells, and more preferably into human cells.

In a preferred method, linear polycationic oligomers are size-selected to substantially neutralize the negative charge of the nucleic acid to facilitate its uptake. In a more preferred method, the polycationic oligomer is size-selected to precisely neutralize the negative charge of the nucleic acid.

Polycationic oligomers having cationic side-groups spaced along the oligomer chain are employed in this method to complex nucleic acid and facilitate its entry into cells. Cationic side groups are spaced in the cationic oligomer to substantially match the spacing between negatively charged groups along the nucleic acid backbone. Preferred oligomers are those which are linear sequential oligomers with cationic side groups on alternating monomer residues along the oligomer chain. Preferred oligomers have cationic side groups spaced to enhance binding to the anionic phosphate or phosphorothioate groups spaced along a nucleic acid chain. Preferred alternating polycationic oligomers for complexation to a nucleic acid are selected to be comparable in size, i.e., in length (number of repeating units), and number of charged side groups to the nucleic acid that is to be introduced into the cell. Preferred oligomers have substantially the same number of cationic groups as the number of anionic phosphate (or phosphorothioate) groups of the nucleic acid.

Polycationic oligomers of a substantially discrete size comparable to that of the nucleic acid can be employed. Alternatively, mixtures of polycationic oligomers of different size, but wherein components of the mixture have a selected range of sizes comparable to the nucleic acid, can also be employed. Preferably the oligomer is selected to be substantially matched (i.e., substantially the same) in length to the nucleic acid to give substantial charge neutralization. More preferably the oligomer is the same length as the nucleic acid, i.e., the number of repeating units of the oligomer (n) is equal to the number of nucleotide bases (b) in the nucleic acid to give precise charge neutralization. Since each repeating unit contains a cationic side group the number of repeating units is equal to the number of cationic side groups in the polycationic oligomer.

The polycationic oligomers useful in the methods of this invention are nucleic acid binding agents. Further, the polycationic oligomers of this invention can be designed to have varying degrees of biodegradability. The oligomers of this invention include peptides and peptoids with amide-linked oligomer chains and oligomers that combine ester- and amide-linked oligomer chains with cationic side groups spaced along those chains. The oligomers are preferentially linear (non-branched) and comprise sequential (i.e., alternating) co-oligomeric regions with cationic side chains on alternating repeating units along the oligomer chain of the region.

In addition to cationic side groups, oligomers useful in the methods of this invention optionally contain side groups capable of being derivatized with selected functional groups at one or more positions along the oligomer chain to incorporate a biologically active group, or an analytical or diagnostic label. A given polycationic oligomer may contain one or more of the same functional groups or may contain different functional groups.

This invention encompasses polycationic oligomers, salts thereof, nucleic acid complexes thereof, uncharged precursors of polycationic oligomers, as well as short oligomers (dimers, trimers, etc.) that are intermediates in the preparation of longer oligomers. The invention also encompasses transfection compositions for cells, particularly eukaryotic cells, which comprise a polycationic oligomer of this invention and a nucleic acid, and which are useful in the improved methods of this invention. Compositions that comprise nucleic acids which are functional in eukaryotic cells, especially in animal, mammalian and human cells, as antisense or antigene agents are of particular interest.

In preferred transfection compositions, polycationic oligomers with cationic side groups are size-selected to substantially neutralize the charge of the polynucleic acid antisense or antigene agent. In more preferred transfection compositions, polycationic oligomers are size-selected, i.e., the number of the cationic side groups is equal to the number of bases in the oligonucleotide to precisely neutralize the charge of the antisense or antigene agent.

In specific preferred transfection compositions, polycationic oligomers with alternating cationic side groups are size-selected to substantially neutralize the charge of the nucleic acid antisense or antigene agent or are size-selected to precisely neutralize the charge, i.e., the number of repeating units in the oligomer (each containing a cationic side group) is equal to the number of bases in the oligonucleotide of the antisense or antigene agent.

In specific embodiments, polycationic oligomers of this invention are tethered to ligands for cell receptors, particularly to ligands for steroid receptors. These ligand-tethered oligomers are particularly useful for targeting of nucleic acid to a selected cell or to a selected site in a cell, e.g. the cell membrane, cell surface or the nucleus. These ligand-tethered oligomers can enhance nucleic acid uptake into selected cells and/or enhance selective retention of the nucleic acid by cells which express the cell receptor to which the ligand-tethered oligomer is targeted.

Polycationic oligomers of this invention are useful generally in any application involving the formation of nucleic acid complexes, i.e., the binding and charge neutralization of the nucleic acid, and are particularly useful in methods for introduction of nucleic acids into cell, in vitro or in vivo, e.g., in methods involving cell transfection, including therapeutic applications of transfection methods to gene therapy, and diagnostic methods. The polycationic oligomers of this invention or their complexes with nucleic acids are also useful in methods of separation and in methods of detection of nucleic acids. Polycationic oligomers of this invention are also useful as research reagents for cell transfection and related laboratory procedures. Methods of this invention include any method in which the polycationic oligomers of this invention are used as nucleic acid binding agents or as charge-neutralization agents.

The improved transfection methods of this invention do not require other transfection agents, such as viral agents, liposomes or cationic lipids. The polycationic oligomers and their complexes with nucleic acids can, however, be employed in combination with compatible art-known transfection agents.

In a specific embodiment, this invention relates to methods of introducing antisense and triplex-forming oligonucleotides into prostate cancer cells to inhibit expression of proteins associated with (or that promote) malignancy and to inhibit cell growth or proliferation. More particularly, the invention relates to a method for inhibiting the expression of the HER-2/NEU protein in prostate cancer cells and to a method for inhibiting prostate cancer cell growth or proliferation. A triplex-forming oligonucleotide, HN28ap or preferably its phosphorothioate analog is introduced into prostate cancer cells to inhibit HER-2/NEU expression as well as to inhibit prostate cancer cell growth or proliferation.

An oligonucleotide that inhibits HER-2/NEU expression can be introduced into prostate cancer cells in culture or in tissue employing transfection methods and well-known carrier molecules. Preferably, inhibitory oligonucleotides are introduced into cells as complexes with polycationic oligomers of this invention. In preferred methods, cells are treated with inhibitory oligonucleotides that are substantially charge neutralized and more preferably with those that are precisely charge neutralized by complexation with size-selected polycationic oligomers of this invention. The methods provided herein can be employed in the treatment of prostate cancer in an animal, including a human. This invention also provides pharmaceutical compositions and dosage forms (e.g., various injectable compositions or compositions suitable for intravenous or intralesional delivery) comprising complexes of antisense or triplex-forming oligonucleotides with polycationic oligomers of this invention.

DETAILED DESCRIPTION OF THE INVENTION

Figure 1:
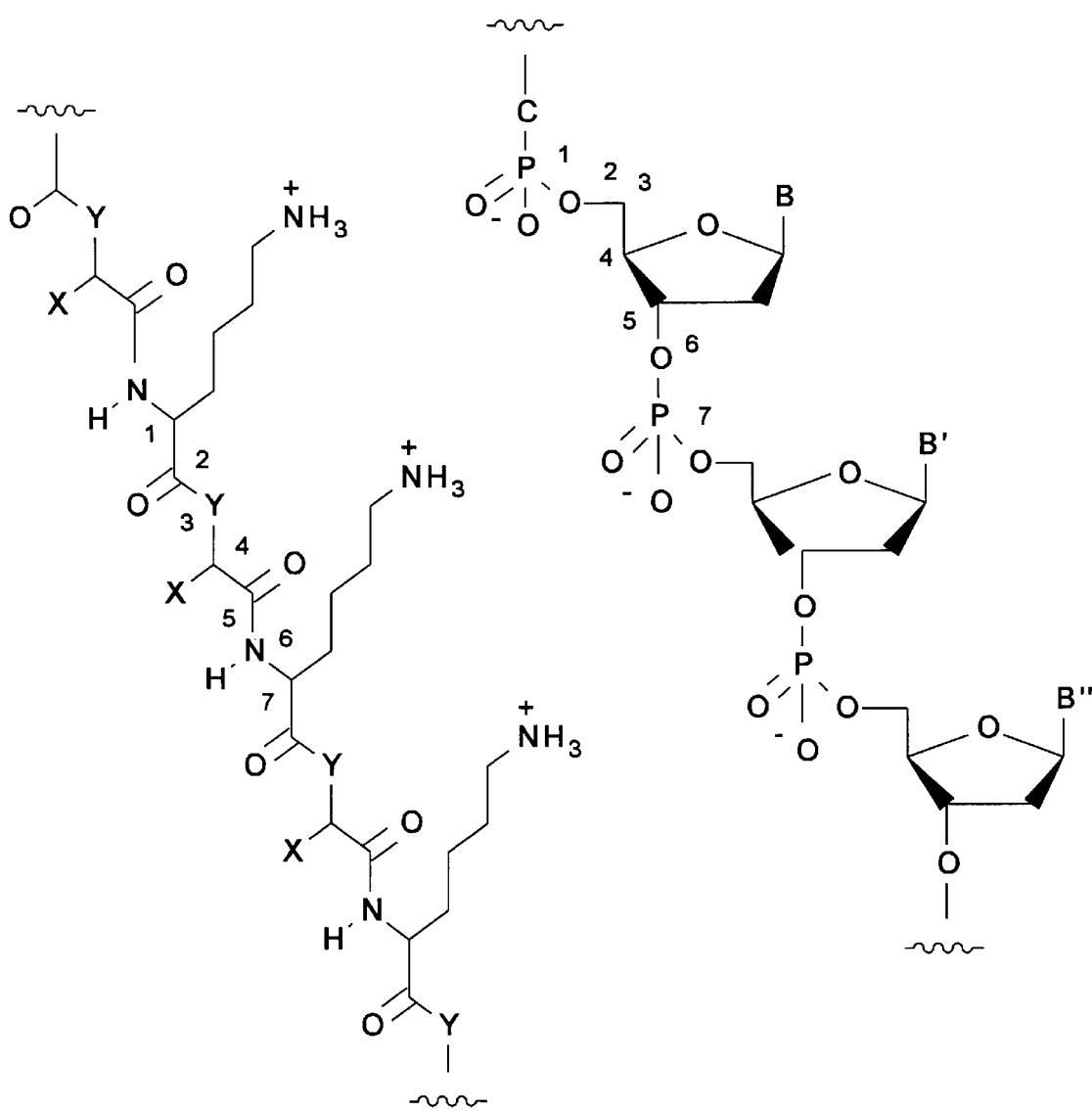
FIG. 1 is a structural representation of a polycationic oligomer-oligodeoxyribonucleotide complex of this invention having repeating unit I.

The polycationic oligomers of this invention include sequential oligomers comprising selectively spaced cationic side groups. The cationic side groups are spaced for binding to the anionic phosphates of nucleic acids. The structures of polycationic oligomers with alternating cationic groups are based on repetitions of a repeating unit (REP) which contains a cationic side group. Additional flexibility for spacing of cationic groups is provided by optional introduction of flexible spacers along the oligomer chain separating regions containing repetitions of REP. The structure of these polycationic oligomers is schematically represented as:

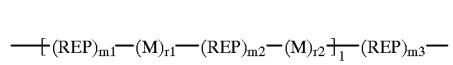

I where REP can be any one of a variety of repeating units containing a cationic side group; m1, m2, and m3 are integers indicating the number of repeating units and 1 is an integer indicating the number of

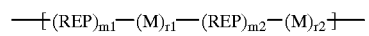

The total number of repeating units in the polycationic oligomer is n which is equal to 1(m1+m2)+m3. The integer n is also the number of cationic side groups in the polycationic oligomer. M is an optional flexible spacer and r1 and r2, independently, are 1 or 0 to indicate the presence or absence of a given spacer in the polycationic oligomer; M is an optional flexible spacer and r1 and r2, independently, are 1 or 0 to indicate the presence or absence of a given spacer in the oligomer. In structure I flexible spacers are inserted between a plurality of repeats of the cationic repeating unit. The spacers are preferably inserted at regular intervals within the repeating structure, but may be selectively inserted at any position to facilitate desired spacing of cationic side groups. In a preferred embodiment, spacers are inserted after each set of 5 REPs.

The optional spacer M preferably comprises a linear chain and has the general formula:

—Z¹—(L)—Z²— where $Z^1$ and $Z^2$, independently of one another, are chemical groups that can form a covalent bond between repeating units and L is a flexible length spacer that is an alkyl group, an ether group or a thioether group. $Z^1$ and $Z^2$, independently, can be groups such as NR (where R is hydrogen or a lower alkyl having 1 to 3 carbon atoms), —CO—, O or —S—. Preferred $Z^1$ and $Z^2$ are NH and CO (where the spacer is derived from an amino acid $NH_2$—L—COOH). The spacer L is preferably an alkyl group, —$(CH_2)_q$— where q is an integer that preferably ranges from 2 to about 10 and more preferably ranges from 3 to about 8. In this alkyl spacer group, one or more non neighboring —$CH_2$— groups can be replaced with an oxygen (—O—) (to give an ether spacer) or a sulfur (—S—) (to give a thioether spacer). An exemplary spacer is —NH—$(CH_2)_5$CO— (6-aminohexanoyl) derived from 6-aminohexanoic acid.

In one aspect, the polycationic oligomers of this invention include sequential oligomers with alternating cationic side groups having the repeating structure II. In a more specific embodiment, the polycationic oligomers of this invention include sequential oligomers with alternating cationic side groups having the repeating structure III. In these structures, M, r1, r2, 1, m1, m2 and m3 are as defined for structure I.

In a polycationic oligomer of structure II, $Y^1$ is O or $NR^3$ and $Y^2$ is O or $NR^4$ and one of $Q^1$ or $Q^2$ in a repeating unit is —$(CH_2)_w$—, where w is an integer ranging from 1 to 3 and the other of $Q^1$ or $Q^2$ in a repeating unit is —CH(R')—. R', $R^3$ and $R^4$ can be H, lower alkyl having from 1–3 carbon atoms, a non-cationic oligomer or a cationic oligomer (as will be described in more detail below), with the proviso that there is only one cationic side group in each repeating unit. Each repeating unit must contain one cationic side group and the cationic side groups alternate along the oligomer chain. Preferred oligomers are linear.

Figure 2:
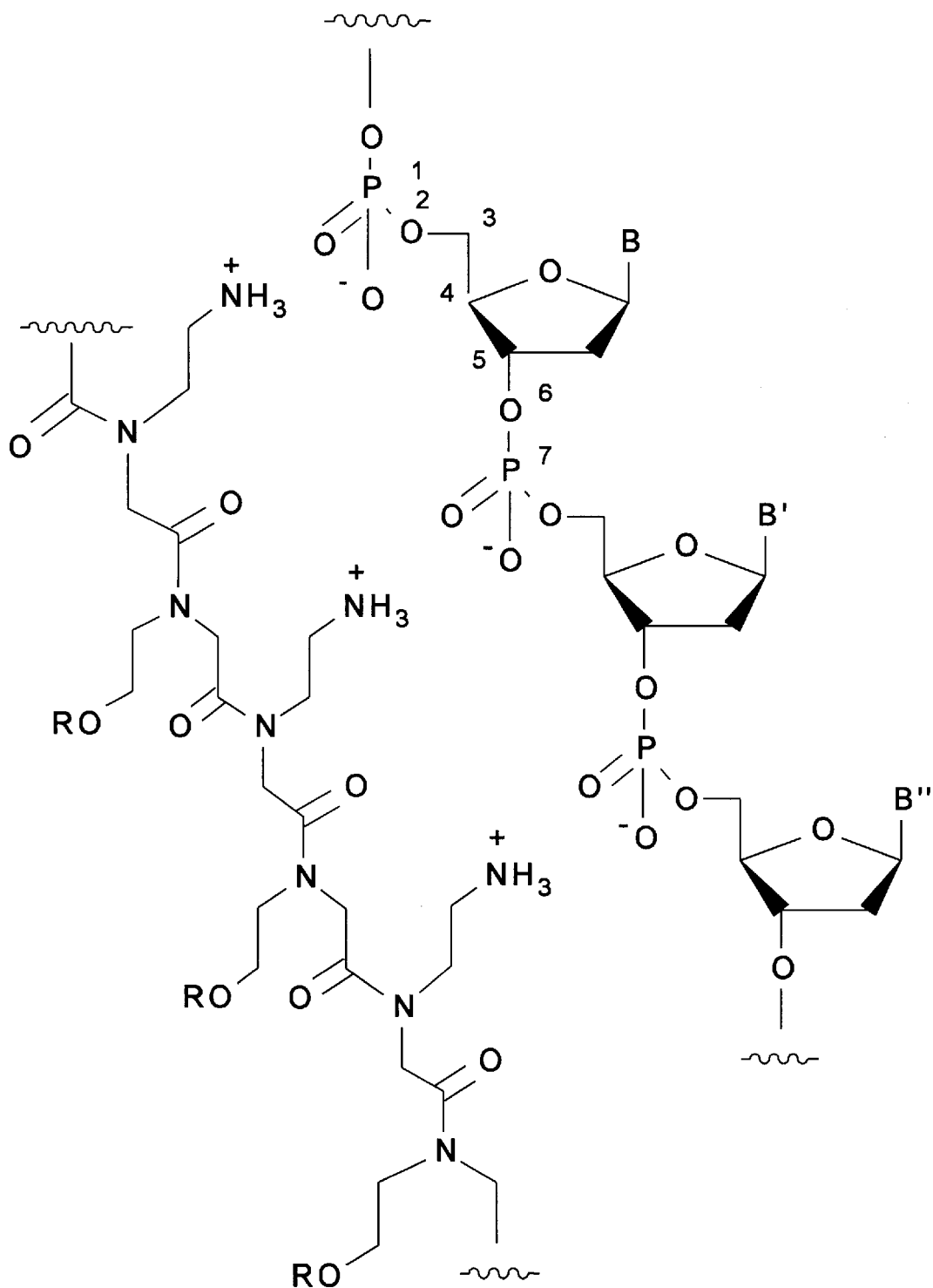
FIG. 2 is a structural representation of a polycationic oligomer(peptoid)-oligodeoxyribonucleotide complex of this invention having formula III.

The cationic side group is a moiety capable of binding to the anionic phosphate or phosphorothioate group of the linkage in nucleic acids, as illustrated in FIGS. 1 and 2.

unsaturated alkyl, or aryl group, or a side group containing a reactive chemical functional group that can be functionalized, such as an alcohol, acid, ester, amine, amide or thiol species, hereinafter called a "tether" side group. $R^1$–$R^4$ in different repeating units need not be the same side group.

One or more of the tether side chains of the repeating units of structures II and III can be derivatized. The oligomers can be derivatized, for example, to incorporate a "tethered" group which, among others, can be a lipid species, a biologically active moiety, such as a steroid hormone, e.g., a sterol, or other cell-receptor ligand, a peptide, peptide hormone, protein or fluorescent or other photochemical label or a radiolabel. Thus, the non-cationic side chain need not be the same in all repeating units in an oligomer. For example, the tether side groups of a given oligomer may be only partially reacted with a lipid, label or biologically functional molecule to generate a tethered group. A given polycationic oligomer of this invention may, for example, contain only one or two tethered side groups.

A wide variety of chemically or biologically active groups can be indirectly complexed to a nucleic acid by first tethering the biologically active group to a polycationic oligomer of this invention. The polycationic oligomer with tethered biologically active group will then complex with the nucleic acid. The side groups can be tethered at any point along the oligomer chain. The polycationic oligomers of this invention can be derivatized at either end or at both ends with a tethered group, for example, a sterol or other biologically functional ligand. After tethering, unreacted tether side groups can be capped or blocked to limit additional reaction and improve chemical stability.

Polycationic oligomers of this invention can also have an end group which can serve as a site for tethering. For example, a non-cationic amino acid, such as a protected cysteine or serine can be bonded to either or both ends of a given polycationic oligomer and may serve after deprotection as a site for covalent bonding of a tethered group.

In a given polycationic oligomer, the repeating units are preferably the same throughout, except in cases where a repeating unit carries a tethered group where it is preferred to include one or two tethered groups in the entire polyca- Structure II:

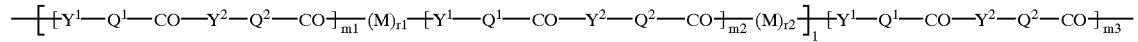

Structure III:

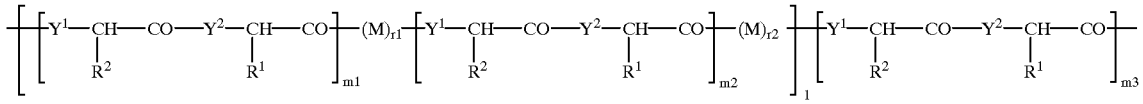

In the polycationic oligomer of structure III, $Y^1$ can be O or $NR^3$ and $Y^2$ can be O or $NR^4$, where one of the side groups $R^1$ or $R^2$ or one of the side groups $R^3$ or $R^4$ in each repeating unit is a cationic side group. The other of $R^1$ or $R^2$, or the other of $R^3$ or $R^4$ in a repeating unit of structure III is a side group that is non-cationic side groups.

In presently preferred embodiments, substantially all the cationic side groups in a given oligomer are the same and substantially all the non-cationic side groups in a given oligomer are the same. The oligomers having this repeating unit may be chiral or achiral. Preferred chiral oligomers are homochiral.

Non-cationic side groups of this invention and can be a nonreactive chemical species, such as a hydrogen, alkyl, tionic oligomer. Repeating units in a given polycationic oligomer may however, be different. For example, the repeating units at the ends of the oligomer may be different from those in the middle of the oligomer.

More specifically, in the polycationic oligomers of this invention with the above structures II and III, preferred cationic side groups are selected from the group —$(CH_2)_t$X where t is an integer from 1 to about 6 and X is a $NH_3^+$ or a —NH—$C(NH_2)$=$NH_2^+$ group. A non-cationic side group can preferably be selected, independently of the groups in other repeating units, from the group consisting of a hydrogen, an allyl group having from 1 to about 6 carbon atoms, a —$(CH_2)_s$—$WR^5$ or a —$(CH_2)_s$—$WR^6$ group, where s is an integer from 1 to about 6, W is an O atom, S atom or a COO, NH, NHCO or CONH group, $R^5$ is a hydrogen or alkyl group having from 1 to 6 carbon atoms, and $R^6$ is a tethered group selected from the group consisting of (i) a ligand for a cell receptor;
(ii) a lipid moiety;
(iii) a hormone peptide;
(iv) a fluorescent label; or
(v) a radiolabel; or
(vi) combination of (i)–(v), each of (i) to (v) can be first appropriately derivatized to facilitate covalent binding to the tether linking group W.

Preferred repeating units of structure II include those of structure II as well as those in which $Y^1$ and $Y^2$ are either NH or O and one of $Q^1$ or $Q^2$ is —CH(R')—, where R' is a cationic side group and the other of $Q^1$ or $Q^2$ is —$(CH_2)_x$— where x is an integer ranging from 1–3, inclusive. An exemplary repeating unit of structure II is:

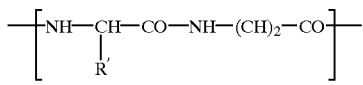

where R' is a cationic side group, particularly a cationic side group side selected from the group —$(CH_2)_tX$ where t is an integer from 1 to about 6 and X is a $NH_3^+$ or a —NH—C$(NH_2)$=$NH_2^+$ group.

Preferred repeating units of structure III are those in which $Y^1$ is $NR^3$, $Y^2$ is $NR^4$ and $R^1$ and $R^2$ are both hydrogens and those in which $Y^1$ and $Y^2$ are O or NH and $R^3$ and $R^4$ are both hydrogens.

In preferred polycationic oligomers of structures I, II and III, the total number of repeating units (n), which is equal to the number of cationic side groups, is selected for a given application for enhanced binding to a nucleic acid to enhance charge neutralization.

In preferred oligomers of structures I–III which contain one or more M spacer groups, m1 and m2 are integers ranging from 4 to 6 and are more preferably 5. In this more preferred structure, a polycationic oligomer comprises regions with alternating cationic side groups interrupted by spacers every 5 repeating units.

When r is 0, polycationic oligomers of structure II have no spacers and can be more simply represented as having the repeating units IIA:

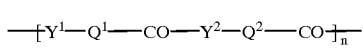

where $Y^1$, $Y^2$, $Q^1$ and $Q^2$ are as defined for structure II and n is the number of repeating units in the polycationic oligomer.

Polycationic oligomers include those having repeating unit IIA where $Y^1$ and $Y^2$ are NH and $Q^1$ and $Q^2$ are as defined for structure II. Polycationic oligomers also include those with repeating unit IIA where $Y^1$ and $Y^2$ are NH, $Q^1$ is —CH(R')—, where R' is a cationic side group, and $Q^2$ is —$(CH_2)_x$—, where x is an integer from 1–3.

When r is 0, polycationic oligomers of structure III have no spacers and can be more simply represented as having the repeating units IIIA:

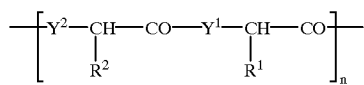

where $Y^1$, $Y^2$, $R^1$ and $R^2$ are as defined for structure III and n is the number of repeating units in the polycationic oligomer.

Polycationic oligomers include those having repeating unit IIIA where $Y^1$ and $Y^2$, independently, are O or NH and $R^1$ and $R^2$ are as defined for structure III. Polycationic oligomers also include those with repeating unit IIIA where $Y^1$ is $NR^3$, $Y^2$ is $NR^4$ and $R^1$ and $R^2$ are both hydrogens.

Specific alternating polycationic oligomers include:

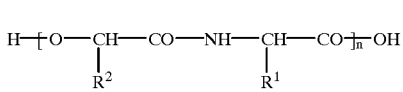

and

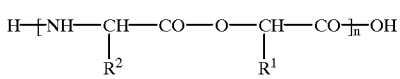

where variables $R^1$, $R^2$ and n are defined as in repeating structure III.

Specific alternating oligomers also include peptides with alternating cationic groups of formula:

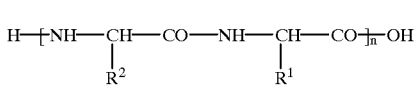

where variables $R^1$, $R^2$ and n are defined as in repeating structure III.

Specific alternating oligomers also include polycationic peptoid oligomers having the formula IV:

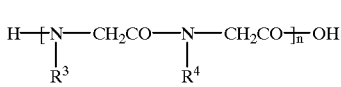

where one of $R^3$ and $R^4$, in each repeating unit, is a side group having a cationic moiety capable of binding to the anionic phosphate or phosphorothioate group of the linkage in nucleic acids as illustrated in FIG. 2. The other of $R^1$ of $R^2$ in a repeating unit is a non-cationic moiety and can be a side group as described above for repeating unit 1 that can be (1) a non-reactive chemical species, (2) a "tether" side chain, (3) a lipid, (4) a chemically, or (5) a biologically active moiety, (6) a label or (7) a combination of side chains 1–6.

Polycationic oligomers of formulas IIIA–E include those where one of $R^1$ or $R^2$, in each repeating unit, is a cationic side group selected from the group —$(CH_2)_tX$ where t is an integer from 1 to about 6 and X is a $NH_3^+$ or a —NH—C$(NH_2)$=$NH_2^+$ group and the other of $R^1$ or $R^2$, in a repeating unit and independently of the side groups in the other repeating units, is selected from the group having from 1 to about 6 carbon atoms, a —$(CH_2)_s$—$WR^5$ group, or a —$(CH_2)_s$—$WR^6$ group, where s is an integer from 1 to about 6, W is an O atom, S atom or a COO, NH, NHCO, or CONH group, $R^5$ is a hydrogen or alkyl group having from 1 to 6 carbon atoms, and $R^6$ is selected from the group consisting of a ligand for a cell receptor, a lipid moiety, a peptide hormone, a fluorescent label or other photochemical label, or a radiolabel any of which may first be derivatized to facilitate linkage to the tether. Preferred cationic side chains for formulas III (A–C) and IV are those in which t is 3 or 4.

Polycationic oligomers of formulas IV include those where one of $R^3$ or $R^4$, in each repeating unit, is a cationic side group selected from the group —$(CH_2)_tX$ where t is an integer from 1 to about 6 and X is a $NH_3^+$ or a —NH—C$(NH_2)$=$NH_2^+$ group and the other of $R^1$ or $R^2$, in a repeating unit and independently of the side groups in the other repeating units, is selected from the group having from 1 to about 6 carbon atoms, a —$(CH_2)_s$—$WR^5$ group, or a —$(CH_2)_s$—$WR^6$ group, where s is an integer from 1 to about 6, W is an O atom, S atom or a COO, NH, NHCO, or CONH group, $R^5$ is a hydrogen or alkyl group having from 1 to 6 carbon atoms, and $R^6$ is selected from the group consisting of a ligand for a cell receptor, a lipid moiety, a peptide hormone, a fluorescent label or other photochemical label, or a radiolabel any of which may first be derivatized to facilitate linkage to the tether. Preferred cationic side chains for formula IV are those in which t is 3 or 4.

Preferred polycationic oligomers of this invention of formulas IIIA–E are those with alternating lysine, arginine, ornithine or homoarginine groups. More preferred cationic side groups are —$(CH_2)_4$—$NH_2$ [or —$(CH_2)_4$—$NH_3^+$ in protonated form, from a lysine residue] and —$(CH_2)_3$—NH—C$(NH_2)$=NH [or —$(CH_2)_3$NH—C$(NH_2)$=$NH_2^+$ in protonated form, from an arginine residue].

Preferred polycationic sequential peptoids of this invention of formula IV are those with alternating N-substituted glycine groups with cationic side groups that are the side chains of the amino acids: lysine (—$(CH_2)_4$—$NH_2$), arginine (—$(CH_2)_3$NH—C$(NH_2)$=NH), ornithine (—$(CH_2)_3$—$NH_2$) and homoarginine (—$(CH_2)_4$NH—C$(NH_2)$=NH) and the 2-aminoethyl group (—$(CH_2)_2NH_2$). These groups are provided by the N-glycine analogues of lysine (Nlys), arginine (Narg), ornithine (Norn), and homoarginine (Nharg), and N-(2-amino)ethylglycine (Naeg).

Preferred polycationic oligomers of this invention have one cationic side group in a repeating unit. The second side group of the repeating unit need not be the same in each repeating unit of the oligomer.

Preferred non-reactive oligomer side groups are hydrogen, methyl, ethyl, propyl and isopropyl groups. In oligomers of repeating unit IIIA where $Y^1$ or $Y^2$ is O, glyoxylic acid (Glx), lactic acid (Lac), 2-hydroxybutyric acid (2HBA), 2-hydroxyvaleric acid (2HVA), and 2-hydroxy-3-methylbutyric acid (2HMBA) can provide these non-reactive side chains, while for $Y^1$ or $Y^2$ that is N, glycine (Gly), alanine (Ala), 2-aminobutyric acid (2ABA), norvaline (N-Val) and valine (Val) groups can provide these non-reactive groups. Polycationic oligomers of this invention with nonreactive side chains include, among others, those with repeating units: [Lys-Lac], [Lac-Lys], [Lys-Gly], [Gly-Lys], [Lys-Ala], [Ala-Lys], [Lys-2ABA], [2ABA-Lys], [Lys-N-Val], [N-Val-Lys], [Lys-Val], [Lys-bAla], [bAla-Lys], [Val-Lys] and those with analogous repeating units in which Lys is replaced with Arg. In these repeating units standard amino acid abbreviations are used, Lac is lactate and bAla is 3-aminopropionoyl (derived from $NH_2$—$CH_2$—$CH_2$—$CO_2H$).

Preferred non-reactive oligomer side groups for oligomers of formulas IIIA–E are alkyls having from 1 to 3 carbon atoms and phenyl (from N-(phenyl)glycine) or benzyl groups (from N-(benzyl)glycine).

In peptoids of formula IV, two N-substituted glycines compose the repeating unit. N-methylglycine (Nala), N-(1-methyl)ethylglycine (Nipr), N-butylglycine (Nbut), N-(2-methyl)propylglycine (Nleu), and N-pentylglycine (Npen) can, for example, supply non-reactive side groups. Polycationic peptoids of this invention include, among others, those with the repeating units [Naeg-Nala], [Nala-Nhaeg], [Naeg-Nbut], [Nbut-Naeg], [Naeg-Nipr], [Nipr-Naeg], [Naeg-Nleu], [Nleu-Naeg], [Naeg-Npen], [Npen-Naeg] as well as the Nlys, Nharg, Norn and Narg analogues of the listed repeating units.

Preferred tether side chains for polycationic oligomers of this invention are —$(CH_2)_sOH$, —$(CH_2)_sCOOH$, (or the corresponding carboxylates), and —$(CH_2)_sNH$—, $(CH_2)_sNH$—CO—, —$(CH_2)_sCONH$— where s is an integer from 1 to about 6. In preferred oligomers of formulas IIIA–E, malic acid (Mal)(via reduction), glutamic acid (Glu), aspartic acid (Asp), serine (Ser) and homoserine (HSer) residues can provide tether side chains. In preferred peptoids of formula IV, N-(2-hydroxyethyl)glycine (Nhser), or N-(4-hydroxy-butyl)glycine (Nhyb) can provide tether groups. Tether side chains may be derivatized to facilitate tethering.

Preferred $R^6$ groups are ligands capable of binding to cell receptors, including cell-surface receptors, cytosolic receptors and receptors that may be associated with the nuclear membrane. Sterol moieties capable of binding to an androgen receptor, such as those found in prostate cells, including cancerous or metastatic prostate cells, are of particular interest. Polycationic oligomers having steroid moieties tethered thereto can target bound nucleic acids to the prostate cells, in particular they can target complexed nucleic acid to the nucleus of such cells. These polycationic oligomers with steroid tethers can also enhance retention of complexed nucleic acid by cells which express the steroid receptor. Many steroid moieties are capable of binding to androgen receptors including, among others, androgens, estrogens, synthetic androgens and estrogens, antiandrogens, and metabolically altered analogues of the forgoing.

Polycationic oligomers of this invention can be employed in the methods of this invention as salts. In general any counterion may be employed with these materials in in vitro applications. Non-toxic counterions should be employed for applications to living cell cultures. For in vivo applications, including antisense and gene therapy and in in vivo diagnostic applications, pharmaceutically acceptable ions are employed, including halides, organic carboxylates, organic sulfonic acid anions and the like. Preferred anions are halogen ions, and most preferably chloride ions.

Preferred polycationic oligomers of this invention are homochiral with substantially all of the oligomer residues in the L-stereoconfiguration to maximize biodegradability. Oligomer residues of polycationic oligomers of formula IV are, however, achiral.

Preferred polycationic oligomers of this invention are those that form nucleic acid complexes that are soluble, particular those that are soluble in pharmaceutically acceptable solvents, such as aqueous solutions including phosphate buffered saline.

Polycationic oligomers of this invention are size-selected to comprise oligomers of substantially discrete size, where preferably about 95% or more of the oligomers in an oligomer sample have a selected discrete length, determined by n the number of repeating units present. Size-selected polycationic oligomers also include mixtures of polycationic oligomers of a selected range of n comparable in size to the nucleic acid to be complexed. In such mixtures of oligomers, preferably about 95% or more of the oligomers in the mixture have n within the range of n comparable in size to the nucleic acid to be complexed. Polycationic oligomers of discrete size n are preferred.

The invention includes transfection compositions comprising polycationic oligomers of this invention and nucleic acid, including compositions comprising complexes of polycationic oligomers of formula IIA, IIIA–E and IV with nucleic acids, wherein the complexes are useful for introducing the nucleic acid into living cells, and/or for selective retention of the nucleic acid by living cells. These complexes are useful for introduction of nucleic acid into various prokaryotic and eukaryotic cells. These complexes are useful, in particular, for introduction of nucleic acid into animal, mammalian, and human cells. The invention also relates to complexes of nucleic acids with polycationic oligomers of comparable length and particularly those complexes in which the polycationic oligomer neutralizes the negative charge of the nucleic acid on complexation. Preferred complexes are those in which the polycationic oligomer has substantially the same number (i.e., substantially matches) of cationic side groups as there are anionic phosphorus (or phosphorothioate) groups in the nucleic acid in which the polycationic oligomer can substantially neutralize the negative charge of the nucleic acid on complexation. More preferred complexes are those in which the polycationic oligomer has the same number of cationic side groups (n) as there are nucleic acid bases (b) in the nucleic acid (i.e. b=n) in which the polycationic oligomer can precisely neutralize the negative charge of phosphorous or phosphorothioate groups of the nucleic acid on complexation.

The term comparable as used herein in relation to the relative sizes of nucleic acid and polycationic oligomer means that the n of the polycationic oligomer ranges from about 1/2b to about 2b, and more preferably from 3/4b to 5/4b. The terms "substantially match" and "substantially the same as," as applied to the relative sizes of polycationic oligomers and nucleic acids, means that n is equal to b±about 15% b, e.g., for a nucleic acid with 56 bases, substantially matched oligomers will have n=56±about 8 or for a nucleic acid of 28 bases substantially matched oligomers will have n=28±about 4.

The invention includes those complexes in which the nucleic acid is an antisense or triplex-forming oligonucleotide (including, among others, deoxyribonucleotides, ribonucleotides and any phosphothioate derivatives thereof) that inhibits gene expression in a cell. Complexes with antisense or triplex-forming oligonucleotides that inhibit undesired protein expression, inhibit undesired cell growth or proliferation, inhibit malignant cell growth or proliferation, inhibit metastasis of malignant cells, or inhibit undesired viral expression are preferred.

Complexes of polycationic oligomers and nucleic acid can be employed in pharmaceutical compositions and dosage units, including various injectable, oral or other dosage forms.

Polycationic oligomers of this invention can generally range in length from several repeating units to several thousand repeating units. More specifically they can range in length from n=2 to about n=2000. Preferred lengths (i.e., n values) depend on the nucleic acid that is to be complexed. Preferred oligomers generally have n greater than about 4 and more preferred oligomers are generally those with n of 10 or greater. Preferred oligomers have n less than about 500 and more preferred have n less than about 100. Shorter polycationic oligomers (n less than about 50, preferably $10 \leq n \leq 50$, more preferably $15 \leq n \leq 35$) are preferred for complexation and transfection of antigene, antisense and triplex-forming agents.

The polycationic oligomers, including those having a tethered group, of this invention are useful in improved methods of introduction of nucleic acids into cells, particularly for introduction of nucleic acids into eukaryotic cells, including animal cells, mammalian cells, insect cells, and the like. Methods of this invention are particularly well suited to use with antigene and antisense agents which are typically nucleic acids with less than about 50 bases and preferably having between about 15–35 bases.

In general, the polycationic oligomer is contacted with nucleic acid under temperature conditions and in media which allow an oligomer-nucleic acid complex to form. Medium components, concentration of nucleic acid and polycationic oligomer, temperature conditions and incubation times for complexation can be readily optimized for any particular polycationic oligomer-nucleic acid pair without the expense of undue experimentation. Preferred methods achieve at least substantial charge neutralization (15% or less of the charge is not neutralized) or precise charge neutralization on complex formation. The oligomer-nucleic acid complex is then contacted with cells under medium and temperature conditions that allow transfection. Similarly, optimal media and temperature conditions and incubation times for transfection can be determined without undue experimentation.

Complexation of the nucleic acid with the oligomer may be improved using pretreatment annealing cycles in which the temperature of the complexation mixture is first raised to disrupt complexation of more weakly bound complexes without disrupting more strongly bound complexes. The temperature of the mixture is then decreased with time, preferably the temperature is slowly decreased with time, e.g., at a rate of 0.5–2° C./min, to facilitate formation of more thermodynamically stable complexes. One or more cycles of annealing may be employed to optimize more thermodynamically stable complex formation.

In general an annealing cycle comprises heating the combined polycationic oligomer and nucleic acid to a first temperature that disrupts complexation of more weakly bound complexes and cooling the heated combination to a second temperature which allows formation of more strongly bound complexes between said oligomer and said nucleic acid. A plurality of annealing cycles may be applied to improve formation of more thermodynamically stable complexes and improve charge neutralization in the complex. In between annealing cycles, the combination is preferably held at the low temperature (typically about room temperature) for several minutes, before raising the temperature to the high temperature (typically about 95° C.) preferably holding there for several minutes before starting the slow cooling of another annealing cycle.

In one aspect of the improved methods of this invention, the sizes (i.e., total number of repeating units n) or range of sizes (i.e., the range of n) of the alternating polycationic oligomer(s) employed are selected to be comparable in size to the nucleic acid to be introduced into the cell (i.e., where n is comparable to the number of bases (b) of the nucleic acid). In a preferred embodiment, the number of repeating units n of the polycationic oligomer is chosen to substantially match the number of bases in the nucleic acid. Polycationic oligomers with alternating cationic side groups in which n is substantially matched to b will give substantial neutralization of the negative charge of the nucleic acid on complexation. Polycationic oligomers with alternating cationic side groups in which n is equal to b will give precise neutralization of the negative charge of the nucleic acid on complexation.

The extent of charge neutralization of a selected nucleic acid on complexation with a selected polycationic oligomer of this invention can be assessed and tested using gel mobility shift assays, for example as described in the examples herein. Temperature, medium and annealing cycles can be optimized for charge neutralized complex formation between a given nucleic acid and size-selected polycationic oligomer employing gel mobility assays.

FIG. 1 is an illustration believed to represent the most stable structure of an alternating polycationic oligomer-nucleic acid complex of this invention. The structure shows three repeating units with three cationic side chains. The cationic side chain exemplified is the —$(CH_2)_4NH_2$ group from the lysine residue, which becomes the cationic species —$(CH_2)_4NH_3^+$ under appropriate aqueous conditions, and which can be isolated as the —$(CH_2)_4NH_3^+$ Z salts, where $Z^-$ is an appropriate counterion. A salt of a polycationic oligomer of n repeating units each with a cationic side group will be associated with n x $Z^-$ counterions. In FIG. 1, Y can be an O or N. When Y is N, the oligomer backbone comprises amide linkages, i.e., a peptide backbone. When Y is O, the oligomer backbone comprises alternating ester and amide bonds. Polycationic oligomers containing ester linkages have enhanced biodegradability compared to oligomers with only amide linkages. As indicated in FIG. 1, the spacing between cationic side groups is substantially the same as the spacing between inter-base phosphate (or phosphorothioate) groups in the nucleic acid. In this representation X can be any of the non-cationic side groups discussed above.

FIG. 2 is an illustration believed to represent the most stable structure of another alternating polycationic oligomer-nucleic acid complex of this invention based on a peptoid structure. The structure shows three repeating units with three cationic side groups. The cationic side group exemplified is the —$(CH_2)_2NH_2$ group, which becomes the cationic species —$(CH_2)_2NH_3^+$ under appropriate aqueous conditions. Cationic oligomers can be isolated as salts with appropriate counterions ($Z^-$). The oligomer backbone comprises substituted amide linkages. As indicated, the spacing between cationic side chains is substantially the same as the spacing between inter-base phosphate (or phosphorothioate) groups in the nucleic acid. The peptoid is exemplified with tethered R groups with a —$CH_2$—$CH_2$—O— tether group.

The actual structure of complexes formed when a nucleic acid and a polycationic oligomer of this invention are mixed together and complexed will depend on the complexation conditions (buffer, salt concentration, temperature and length of incubation, etc.) employed. A variety of structures of nucleic acid-oligomer complexes may be present in mixtures prepared for use in transfection or other applications of this invention.

The polycationic oligomers with spaced cationic side groups of this invention exhibit enhanced binding affinity for nucleic acids compared to polylysine, polyarginine or related polycationic oligomers and compared to non-cationic polypeptides, peptoids and related oligomers and random copolymers. In particular, the sequential polycationic oligomers of this invention with alternating cationic side groups along the oligomer backbone have enhanced binding affinity for nucleic acids compared to non-alternating polycationic oligomers and random copolymers containing cationic side groups.

Although not wishing to be bound thereby, it is believed that the generally enhanced affinity of the alternating polycationic oligomers of this invention for nucleic acids compared to prior art polycations, including polylysines and random co-polymers containing lysine or arginine, is the result of matching the spacing of cationic side chains in the polycationic oligomers to the spacing of charged phosphate (or phosphorothioate) groups in the nucleic acid which leads to more efficient charge neutralization of the nucleic acid.

Polycationic oligomers of this invention display enhanced affinity for nucleic acids of comparable length, i.e. the number of nucleic acid bases "b" (one phosphate or phosphorothioate linkage/base) in the nucleic acid is comparable to the number of repeating units n in the oligomer, compared to their affinity for longer or shorter nucleic acids. Affinity between a polycationic oligomer and a nucleic acid generally increases as the spacing and number of the cationic groups in the polycationic oligomer is more closely matched to the spacing and number of the anionic phosphate or phosphorothioate links in the nucleic acid.

Dependent upon the nucleic acid to be complexed, polycationic oligomers of this invention include those with repeating unit I, where n is an integer from 2 to about 2,000. Oligomers for binding nucleic acid also include those in which n is 4 to about 500, as well as those with n between about 10 and about 100. This invention includes mixtures of oligomers with varying n, where n of component oligomers can range from 4 to about 2,000. This invention also includes compositions of oligomers of substantially discrete size, with substantially all of the oligomers having substantially the same length (i.e., having substantially the same n). The term "substantially" as used with respect to the size of oligomers in a sample means that at least about 80%, and preferably 90% or more of the oligomers in a sample are the same length. For discrete sized oligomers, preferred n range most generally from 4 to about 500. More preferred oligomers have n of about 10 to about 100.

Enhanced binding affinity of sequential polycationic oligomers with alternating cationic side groups for nucleic acids results in enhanced transfection efficiencies when polycationic oligomers are at least comparable in size to nucleic acids to be introduced into cells.

In general, polycationic oligomers more useful for binding nucleic acids for their introduction into cells are those with n ranging from about 10 or more. Shorter oligomers, those of n=2 to about 10 are generally more useful in the synthesis of longer oligomers.

Preferred polycationic oligomers of this invention are biodegradable. In applications where oligomers are used in vivo to carry nucleic acids into cells, the polycationic oligomer carrier should be capable of being degraded into non-toxic components by endogenous proteases and esterases to release complexed nucleic acid. Dependent upon the application of a polycationic oligomer of this invention, it may be desirable to use polycationic oligomers that are more or less biodegradable. The oligomers of this invention can be selected to be more or less biodegradable by varying the ester content of the oligomer backbone. Preferred oligomers of this invention are homochiral, i.e. have monomer residues that have the same stereoconfiguration. Preferred biodegradable oligomers have residues with L-configurations.

Polycationic oligomers of this invention are believed to be more biodegradable than polylysine oligomers. Enhanced biodegradability of a nucleic acid carrier can result in improved release of the complexed nucleic acid after its introduction into a cell.

For certain applications it may be desirable to employ fully or partially non-biodegradable oligomers. Nonbiodegradability can be enhanced by use of D-configuration residues.

The affinity of polycationic oligomers of this invention for binding to nucleic acids can be assessed by methods well-known in the art.

In one aspect, this invention relates to an improved method for transfecting cells, particularly eukaryotic cells, (in vivo or in vitro) with nucleic acids by complexing the nucleic acid to be introduced into the cell with a polycationic oligomer such that the charge of the nucleic acid is sufficiently neutralized to allow passage, preferably, but not necessarily exclusively, by diffusion into the cell. Once the complexed nucleic acid is inside of the cell, the polycationic oligomer can be degraded by endogenous proteases or esterases releasing the nucleic acid.

Most generally, the term transfection is used herein to mean introduction of nucleic acid into a cell. For practical applications, the nucleic acid should preferably be introduced into the cell substantially retaining its desired biological function within the cell. Nucleic acids can have a variety of biological functions in a cell. They can, for example, be expressible nucleic acids, which encode a peptide or protein that will be expressed in the cell. They can, for example, inhibit or enhance endogenous expression or viral expression in the cell. They can, for example, inhibit protein function or cell growth or proliferation. They can, for example, catalyze reactions or serve in a diagnostic application. Transfection efficiency can most simply be measured by determining, using radioactive labeling techniques, for example, the amount of polynucleic acid that is introduced into cells. This method does not assess functionality of the nucleic acid introduced. Transfection can be, and is often, measured by assessing the biological function, e.g., expression, inhibition or catalysis, of the nucleic acid in the cell.

In applications to diagnostics mediated by a transfection step, transfection can be assessed indirectly by examining the reliability and sensitivity of the diagnostic application. Transfection can be assessed either by the level of stable or transient biological function in the cell due to the presence of the nucleic acid introduced. In cases where an expressible nucleic acid is introduced into a cell, either stable or transient expression of the nucleic acid can be assessed. In the case of nucleic acids that are inhibitory, transfection efficiency can be assessed by measuring the extent of inhibition due to the presence of nucleic acid in the cell.

The terms nucleic acid and oligonucleotide are used generally and interchangeably herein and include both DNA (deoxyribonucleic acids) and RNA (ribonucleic acids) generally without limits to size (except as indicated in specific preferments listed herein) and source and may include natural or non-natural bases. Standard abbreviations for nucleic acid bases are used herein. Of particular interest in the methods of this invention are relatively short nucleic acids, less than about 100 bases in length and more typically 30 or fewer bases in length, which function as antisense or antigene agents. The terms include nucleic acids including commonly occurring bases: A,T,U, C and G as well as less common bases including derivatives and analogues of commonly occurring bases, xanthine and inosine. The terms also include analogues, such as phosphorothioates and related analogues, which can be less susceptible to degradation in vivo.

In a preferred embodiment, transfection compositions of this invention contain only nucleic acid and polycationic oligomer in an appropriate, typically buffered, aqueous medium. The amount of polycationic oligomer contained in the transfection composition is preferably present in excess of the amount of nucleic acid present to ensure that substantially all of the nucleic acid is complexed with the oligomer.

Transfection compositions may optionally contain other ingredients known in the art to enhance transfection or cell growth, if desirable, which are chemically and biochemically compatible with the nucleic acid and polycationic oligomer and which do not disrupt complexation of the oligomer with the nucleic acid. For example, transfection compositions may include cell growth factors. The polycationic oligomer-nucleic acid complexes of this invention may also be used in combination with other known transfection techniques, such as liposome technology or cationic lipid technology, to further enhance transfection efficiency.

Table 1 exemplifies a number of protected repeating units which can be used in the synthesis of certain polycationic oligomers of this invention. Oligomers having the same repeating unit can be synthesized starting with monomers in which the residues are in reversed order. For example, in the [Lys-Lac] repeating unit the residues are linked by an ester linkage and the repeating unit is linked to other repeating units via amide bonds. In contrast, the [Lac-Lys] repeating unit has an internal amide bond and repeating units are linked by ester bonds. The syntheses of oligomers from reversed repeating units are different as shown in Schemes 1A, 1B and 2, but the resulting oligomers have the same repeating unit with the same number of amide and ester linkages. The only difference in the oligomers with reversed order of monomer residues is the relationship of the repeating unit groups to the ends of the oligomer. In oligomer [Lys-Lac]$_n$ one end of the oligomer will have an amine group and the other end an acid group, while in oligomer [Lac-Lys]$_n$, one end has a hydroxy and the other end an ester group. It may be necessary or desirable to cap or protect the termini of any polycationic oligomers of this invention to prevent undesired reaction with the terminal groups.

The synthesis of polycationic oligomers having repeating unit IIIA and in which $Y^1$ or $Y^2$ is O are exemplified in Scheme 1A for the synthesis of the repeating unit [Lys-Lac] and in Scheme 2 for the synthesis of the reversed repeating unit [Lac-Lys]. The polycationic oligomers derived from the repeating units prepared via Scheme 1A and 2 are composed of an amino acid with a cationic side chain (natural or synthetic) and an α-hydroxy acid, such as lactate (Lac) or 2-hydroxybutyric acid (2HBA). Compounds of repeating unit I, in which $Y^1$ or $Y^2$ is O, other than those containing lactate, with appropriate protecting groups, can be readily synthesized by methods of Schemes 1 and 2 or by routine modification of these methods in view of what is well-known in the art by choice of starting materials, protecting group or reaction conditions. Starting materials for preparation of polycationic oligomers of repeating unit IIIA where Y is O are readily available from commercial sources or by routine synthesis from commercially available materials.

As indicated in these schemes, a protected monomer (containing two linked residues) is selectively deprotected and employed in solid phase peptide synthesis (SPPS) to prepare protected oligomers which can then be deprotected and purified by conventional methods. As indicated in the examples, standard SPPS methods have been modified to optimize synthesis of the oligomers of this invention which have highly repeating structures.

Scheme 1B illustrates coupling of two selectively deprotected monomers to form a protected dimer. The dimer may be used to prepare higher oligomers.

Polycationic oligomers having repeating unit IIIA in which $Y^1$ and $Y^2$ are N are peptides synthesized by literature methods, for example, according to methods described in Kubota, S. et al. (1983) supra (1) and (2); Brach, A. and Caille, A. (1978) supra; Barbier, B. et al. (1984) supra, or by routine modification of such methods in view of the description herein and what is well-known in the art. Alternating peptides can be synthesized by sequential addition of appropriately protected and activated amino acids to a growing peptide oligomer on a solid support. Another method of synthesis of H-[Lys-Ala]$_n$—OH is illustrated in Scheme 3 and described in the Examples. In this alternative method, dipeptides (i.e., comprising the repeating unit) are sequentially added to a growing peptide oligomer on a solid support.

Repeating units of these peptide polycationic oligomers are dipeptides combining (1) two of the twenty common amino acids, e.g., [Lys-Ser], (2) one common amino acid and one rare or synthetic amino acid, e.g., [Lys-2ABA], or (3) two rare or synthetic amino acids, e.g., [Orn-2ABA]. All of these combinations of repeating units, with appropriate protecting groups, can be readily synthesized by known methods in view of the disclosure herein with appropriate choice of starting materials. Starting materials for preparation of polycationic oligomers of repeating unit IIIA where $Y^1$ and $Y^2$ are N are readily available from commercial sources or by routine synthesis from commercially available materials.

Repeating units can be deprotected and coupled to form repeating unit dimers by well-known literature methods. Trimers and tetramers of the repeating unit and higher oligomers can also be prepared by well-known methods. Well-known methods of solid phase peptide synthesis can be applied to the synthesis of oligomers of desired n, particularly to those oligomers where n is about 50 or less. Methods for isolation and purification, if desired, of oligomers of certain discrete n or mixtures having a selected range of n are well-known in the art.

Polycationic oligomers of this invention that are alternating (i.e., sequential) peptides can also be prepared by recombinant DNA methods via expression of synthetic coding sequences.

Schemes 4, 5A and 5B illustrate methods for synthesis of tethered monomers. In Scheme 4 methods for tethering a sterol (DHT) to glutamic acid are exemplified. The DHT-derivatized acid is coupled to lysine (a cationic residue). In one method, 3-amino-DHT is coupled to the glutamic acid side chain by an amide or amine linkage. In another method, DHT may be coupled to the reduced glutamic acid side chain (an alcohol).

Schemes 5A and 5B illustrate methods for tethering a sterol to malic acid. Monomers having a tethered group can be employed in SPPS to form polycationic oligomers. These monomers can also be introduced into polycationic oligomers comprising different monomers using SPPS methods.

Scheme 6 illustrates methods for introducing spacers at the 3-amino position in DHT, a sterol, to facilitate tethering. These methods are examples of derivatization of the tether group prior to coupling to the tether side-chain of the oligomer. These methods can be readily adapted for use with a variety of tether groups, most particularly they are useful in tethering sterols to polycationic oligomers.

Steroid moieties are the preferred cell receptor ligands of this invention for tethering to polycationic oligomers and for nucleic acid targeting. The methods of Schemes 4, 5A–5B and 6 or routine adaptation of those methods may be employed to prepare polycationic oligomers conjugated via a tether to various steroid moieties. Steroid moieties can be tethered to the polycationic oligomers of this invention via coupling to tether side groups, such as —(CH$_2$)$_n$—OH, —(CH$_2$)$_m$—COOH, —(CH$_2$)$_p$—NH$_2$, —(CH$_2$)$_q$—C(O)NH$_2$ or (—(CH$_2$)$_r$—NH—C(O)— groups where n, m, p, q and r are integers, preferably ranging in value from 1 to 6 (such as those of, or derived from, Ser, HSer, Glu, Asp, Nser, Nhser, Nasp, or Nglu monomer residues) using conventional synthetic techniques. The steroid can be derivatized or chemically modified prior to tethering to facilitate covalent bonding. For example, sterols can be provided with spacer groups to increase the length of the tethered sterol to the oligomer. Steroid moieties which bind to androgen receptors and which are suitable for use in ligand conjugates of this invention include: dihydrotestosterone (DHT), testosterone, estradiol, progesterone, androstanediol, androstenedione, hydroxyandrostendione, mibolerone, cortisol, methyltrienolone, promegestone, triamcinolone acetonide, cyproterone acetate, hydroxyflutamide, nilutamide, casodex, tamoxifen, and 17β-hydroxy-17α-methylestra-4,9,11-triene-3-one (R188). A preferred steroid moiety is dihydrotestosterone.

Preferably, the polycationic oligomer is attached at C-3 or C-20 (as defined by standard steroid nomenclature and understood in the art). One or more of the steroid moieties are linked via tether side chains in the polycationic oligomer. The preferred linkages are ether, ester, amine or amide linkages. It will be understood that steroid moieties, including those listed above, can be derivatized or otherwise chemically modified to facilitate linkage to the tether. It will be understood that such methods must not significantly interfere with binding of the steroid to its receptor.

In preparation of oligomers with tethered steroid moieties, the polycationic oligomer is covalently linked to the steroid moiety at a site on the steroid that does not significantly interfere with its binding to the targeted receptor, e.g., the androgen receptor. The synthesis illustrated in Schemes 4 and 5A–B, link the steroid via the 3 position.

The polycationic oligomers of this invention can be used in separation, diagnostic or analytical applications in which the oligomer is attached to a surface or a solid support. A tethered group can provide for attachment to such solid supports or surfaces.

Preferred tethers for attachment to surfaces or solid supports are generally non-reactive under the conditions of the application, and preferably selectively removable. Tethers formed from alkyl, alkenyl or aryl chains linked via appropriate functional groups to the surface and the oligomer are preferred. A variety of reagents are known and used for linking materials to solids and surfaces. These linking agents, including siloxanes and related silicon-based linking agents, can be employed with the oligomers of this invention.

Polycationic peptoids of formula IV are synthesized by literature methods, well known in the art. The synthesis of peptoids of this invention is illustrated by the synthesis of Scheme 7. The scheme illustrates the sub-monomer and monomer methods of making peptoids on solid support (P). It may be necessary to adapt reaction times and conditions to optimize coupling and any deprotection steps for synthesis of the highly repeating peptoids of this invention. In the monomer method, appropriately protected peptoid monomers, various N-substituted glycines, are sequentially reacted with a growing peptoid chain on a solid support. Note that coupling of two N-substituted glycine monomers gives the repeating unit of formula III. In the sub-monomer method, discrete repeating units are not separately synthesized. α-Bromoacetic acid is coupled onto the support, for example via an amine group on the solid support. Bromoacylated support is then reacted with a substituted amine to generate the repeating unit moiety on the support. These steps are repeated until the product of desired length (number of repeating units, n) is obtained. The amine is, for example, an alkyl amine, or a mono-Boc-protected diamine with $C_1$–$C_4$ chain or for tethering $H_2N$—$(CH_2)_n$—$R^6$, where n is an integer preferably having a value less than about 10 and more preferably where n=1 to 4 and where $R^6$ is as defined above in the description of structures I, II and III. In particular, $R^6$ can be a steroid such as those listed above.

For monomer synthesis of peptoids, see: H. Kessler (1993) Angew. Chem. Int. Ed. Engl. 32:543–544; G. B. Fields and R. L. Noble (1990) Int. J. Pept. Protein Res. 35:161–214. Peptoid monomers, with appropriate protecting groups, are prepared by literature methods, for example as in A. M. Mouna et al. (1994) Synthetic Comm. 24(17) :2429–2435 and references cited therein. For sub-monomer synthesis of peptoids, see: R. N. Zuckermann et al. (1992) J. Am. Chem. Soc. 114:10646–10647; R. N. Zuchermann et al. (1994) J. Med. Chem. 37:2678–2685. J. A. W. Kruijtzer and R. M. J. Liskamp (1995) Tet. Letts. 36:6969–6972 describes solution synthesis of peptoids using Fmoc-protected N-substituted glycines. Each of these methods, or any appropriate combinations thereof, can be employed, alone or in combination with other synthetic methods known in the art, to synthesize peptoids of this invention.

Tethered groups can be introduced into the peptoid oligomers of this invention by use of a derivatized tether group, such as compound 52, which can be employed as a monomer residue in peptoid synthesis.

The polycationic oligomers of this invention are useful in methods for introducing nucleic acids into cells. Nucleic acids of selected sequence are typically prepared by standard well-known techniques. Methods for the incorporation of non-standard bases or reported groups, such as fluorescent groups or biotin, into nucleic acids are also well-known in the art. Deoxyribonucleotides, for example, can be prepared using solid-phase methodology utilizing the phosphoroamidite approach (Beaucage, S. L. (1993) "Oligodeoxyribonucleotides synthesis. Phosphoroamidite approach." *Meth-ods Mol. Biol.* 20:33–61). Methods for the preparation of various nucleic acid analogues are also well-known (S. Agrawal, (ed.), (1993) *Methods in Molecular Biology*, Vol. 20: "Protocols for Oligonucleotides and Analogues," Humana Press, Inc. Totowa, N.J., including pages 33–61).

Conditions for cell transfection are generally known in the art. In may be necessary to adjust particular conditions for a given polycationic oligomer, nucleic acid and cell type. Such adjustments can be readily made without expense of undue experimentation. Compositions for nucleic acid delivery and targeting employing polycationic oligomers with tethered groups, such as steroids, can be prepared employing methods known in the art, such as those methods described for polylysine in pending U.S. patent application Ser. No. 08/283,238. Adjustment of relative concentrations of polycation and nucleic acid is readily made to ensure optimal complexation of the nucleic acid. Adjustment of temperature and complexation time and the use of cycles of annealing may be needed to optimize complex formation with polycationic oligomers. Specific procedures and techniques for contacting cells with nucleic acid complexes are well known in the art.

In general, a selected polycationic oligomer is combined with the nucleic acid in buffer at a temperature and for a time chosen to optimize complexation of the oligomer with the nucleic acid. The complexed nucleic acid is then contacted with cells again at a temperature and for a time chosen to optimize introduction of the nucleic acid in the cells.

The extent of complexation of nucleic acids can be assessed by electrophoretic gel mobility shift assays. Such assays can be used to optimize relative concentrations of polycationic oligomers and nucleic acid, buffer, incubation temperature and incubation time for complexation and charge neutralization. The amount of polycationic oligomer employed to complex a given nucleic acid is preferably sufficient to neutralize the charge of the nucleic acid, an excess over the equimolar amount of oligomer to nucleic acid being preferred. It may be necessary to adjust concentrations, buffer, temperature and incubation time for different nucleic acids and oligomers. Such optimization in view of the teachings herein is routine in the art.

Nucleic acid uptake by cells can be assessed using standard radiolabelling and scintillation counting techniques. After incubation with radiolabelled nucleic acid-polycationic oligomer complexes, cells are washed to remove exogenous complexes and assessed for radiolabel uptake. Such uptake assays can be used in general to optimize conditions for transfection of nucleic acid complexes into cells. The concentration of complex, buffer, temperature and incubation time can all be readily optimized using uptake assays. Such optimization is routine in the art.

Transfection of functional nucleic acid can be assessed by any of a variety of assays which measure that function. It may be necessary to adjust transfection conditions to optimize introduction of functional nucleic acid. Such optimization is routine in the art.

In a specific embodiment, this invention provides a method for inhibiting expression of certain proteins in prostate cancer cells. In general, the method comprises the step of introducing into prostate cancer cells a nucleic acid that inhibits the expression of a selected gene in the cell. The nucleic acid preferably inhibits the undesired expression of a gene in the transformed cell, particularly of a gene that is associated with malignancy of the cell, undesired cell growth or cell proliferation. Preferred nucleic acids are antisense and antigene agents, including triplex-forming agents that inhibit expression of proto-oncogenes or oncogenes.

The invention relates more specifically to inhibition of HER-2/NEU protein expression in prostate cancer cells by introduction of a triplex-forming nucleic acid that binds to the promoter region of the her-2/neu gene. A purine-rich (G and A) region of the her-2/neu promoter has been identified as a potential target for inhibition by triplex-forming oligonucleotides. A triple target sequence in her-2/neu promoter region:

5'AGGAGAAGGAGGAGGTGGAGGAGGAGGG 3' (SEQ ID NO: 2)

3' TCCTCTTCCTCCTCCACCTCCTCCTCCC 5' (SEQ ID NO: 3)

has been identified extending from −42 to −69 relative to the major transcription start (Ebbinghaus S. W. et al. (1993)). The oligodeoxynucleotide HN28ap (human neu 28-mer antiparallel, i.e., reversed in orientation with respect to the genomic target) having the sequence:

5'-G GGA GGA GGA GGT GGA GGA GGA GGA GGA-3' (SEQ ID NO: 1)

was reported to form triplexes with the her-2/neu target site.

It has been suggested that the T in the HN28ap sequence will destabilize triplex-formation and should be replaced with an abasic linker group of appropriate size to match the normal spacing of bases in the sequence (Ebbinghouse S. W. et al. (1993) supra). It has also been suggested that the destabilizing T in the sequence should be replaced with a C to improve triplex formation. Results of the present work indicate that the HN28ap sequence, at least when the phosphorothioate derivative is employed, functions for inhibition of HER-2/NEU expression in living prostate cancer cells.

In view of these results, preferred triplex-forming nucleic acids for introduction into cells are phosphorothioate derivatives of single-stranded deoxyribonucleotides. Efficient introduction of HN28ap into prostate cancer cells was obtained by initial complexation of HN28ap with a size-matched polycationic oligomer $(KA)_{28}$ ($[LysAla]_{28}$, where n=b=28) followed by incubation of the complex with the cells. Introduction of the phosphorothioate derivative of HN28ap triplex-forming nucleic acid into prostate cancer cells in culture significantly inhibits HER-2/NEU expression. This triplex-forming agent is also useful for inhibiting prostate cancer cell growth and proliferation in vitro and in vivo.

Nucleic acid analogues, derivatives, truncations and extensions of HN28ap, particularly those which are phosphorothioates, that retain site-specific triplex-formation in the her-2/neu promoter region can be employed for inhibition of HER-2/NEU protein expression in prostate cancer cells and more generally for inhibition of growth and/or proliferation of prostate cancer cells. Useful derivatives of HN28ap include those in which the pyrimidine T (at position 13 in SEQ ID NO: 1) is substituted with another natural or non-naturally occurring base or with an abasic spacer moiety. Further useful derivatives of HN28ap are those nucleic acids with short truncations of up to about four bases at the 3'- and/or 5'-ends of the nucleic acid which do not significantly effect triplex-formation ability. Preferred triplex-forming agents have at least 20 bases. Similarly, derivatives of HN28ap with short sequence extensions at the 3'- and/or 5'-end, preferably with sequence consistent with the target site sequence, are useful in this invention. Preferred triplex-forming agents have 40 or fewer bases. The method for inhibition of HER-2/NEU protein expression can be applied to prostate cancer cells in culture or in vivo in tumor tissue.

This invention includes pharmaceutical compositions containing polycationic oligomer-nucleic acid complexes, particularly those comprising HN28ap (or functional triplex-forming analogues, derivatives, extensions and truncations thereof) and a size-selected polycationic oligomer of this invention in a pharmaceutically acceptable carrier, for example, aqueous solutions (including buffered saline), oil-based carriers or emulsions. Pharmaceutical compositions optionally include components that, for example, effect solubility of active ingredients, control pH, stabilize the active ingredients or convey similar useful properties.

In preferred pharmaceutical compositions, the HN28ap phosphorothioate is complexed to a polycationic oligomer substantially matched in length (i.e., n=24–32 when b=28) and the complex is substantially charge neutralized. More preferred pharmaceutical compositions comprise complexes of triplex-forming nucleic acids with size-matched (n=b) polycationic oligomers wherein the complex is precisely charge neutralized.

Complexes of triplex-forming nucleic acid and polycationic oligomer effective for inhibition of prostate cancer can be provided in a variety of dosage forms for therapeutic applications. For example, injectable formulations and formulations for intravenous and/or intralesional administration containing these complexes can be used in prostate cancer therapy.

Inhibitory nucleic acid therapies can be combined to obtain an improved therapeutic result. For example, two or more different antisense, antigene or triplex-forming oligonucleotides can be combined in the same pharmaceutical composition for administration to inhibit cancer cells.

Nucleic acids of this invention include salts thereof, particularly pharmaceutically acceptable salts, e.g., sodium, magnesium, ammonium salts and the like.

In general the pharmaceutical compositions of this invention should contain sufficient inhibitory nucleic acid to result in an inhibitory level of the inhibitory nucleic acid in the target cells. Where a polycationic oligomer is employed as a carrier, the pharmaceutical composition should preferably contain sufficient levels of oligomer to neutralize the negative charge of any oligonucleotides present.

The cellular level of nucleic acid that will be inhibitory will depend on the efficiency of inhibition, e.g., for triplex-forming oligonucleotide the binding affinity, and on the number of sites that must be inhibited or neutralized by the inhibitory nucleic acid. An important consideration in designing oligonucleotide-based therapy is the number of target molecules or sites which must be "neutralized" for the desired effect to occur. In antisense oligo therapy, each messenger RNA molecule must interact with an oligonucleotide to prevent translation. In contrast, in oligo therapy based on triplex formation, it is expected that there will be many fewer target sites in genomic promoters that must interact with the therapeutic oligonucleotide in order to obtain the desired inhibition. As a consequence, it is expected that lower intracellular concentrations of therapeutic triplex-forming oligonucleotides are required compared to antisense oligonucleotides.

The dosage of triplex-forming nucleic acid and/or its complex with polycationic oligomer administered to a patient will also depend on a number of other factors including the method and site of administration, patient age, weight and condition. Those of ordinary skill in the art can readily adjust dosages for a given type of administration and a given patient.

It will be appreciated by those of ordinary skill in the art that the transfection composition should contain minimal amounts of inhibitory components, such as serum or high salt levels, which may inhibit complexation of nucleic acid with polycationic oligomer, interfere with diffusion or any other mechanism of introduction of the complex into the cell, or otherwise interfere with transfection or nucleic acid complexation. It will also be appreciated that any pharmaceutical or therapeutic compositions, dependent upon the particular application, should contain minimal amounts of components that might cause detrimental side-effects in a patient.

The following examples illustrate the invention and are in no way intended to limit its scope.

EXAMPLES

Standard abbreviations are used in the examples for amino acids, protecting groups, reagents and solvents. Abbreviations used include: bAla, 3-aminopropionyl; Boc, tert-butyloxycarbonyl; Cbz, 2-chlorobenzyloxycarbonyl; DCM, dichloromethane; DIEA, diisopropylethylamine; DMAP, dimethylaminopyridine; eACA, 6-aminohexanoyl; EDAC, 1-ethyl-3-(3-dimethylaminopropyl)carbodiimide HCl; Fmoc, 9 fluorenylmethoxycarbonyl; HOBt, 1-hydroxybenzotriazole; NMP, N-methylpyrrolidone; NPYS, 3-nitro-2-pyridinesulphenyl; tBu, tert butyl; TFA, trifluoroacetic acid; THF, tetrahydrofuran and EtOAc, ethyl acetate; Bn, benzyl; DMF, N,N-dimethylformamide; In the following examples all alpha-amino acids are in L-configuration unless otherwise indicated.

Example 1

Synthesis of H-[Lys-Lac]$_n$-OH by reference to Scheme 1A and B

Synthesis of (S)-benzyl lactate 2

Commercially available L-lactide 1 (16 g, 0.14 mol) and p-toluenesulfonic acid monohydrate (catalytic amount) in benzyl alcohol (40 mL, 0.38 mol) was heated to 110° C. overnight. Excess benzyl alcohol was removed under vacuum to obtain a light yellow oil. The desired product was distilled under vacuum (0.9 mm Hg, 85–95° C.) to obtain 50.3 g of 2 as a clear oil. The distilled oil was used without further purification.

Synthesis of Fmoc-Lys($^t$Boc)-Lac-OBn 4

Commercially available Nα-Fmoc-Nε-t-Boc-L-lysine 3 (9.8 g, 21.09 mmol), (S)-benzyl lactate 2 (4.4 g, 24.4 mmol) and dicyclohexylcarbodiimide (DCC, 4.2 g, 23.4 mmol) in dichloromethane (~200 mL) was stirred at room temperature overnight. The resulting white solid was filtered off and was washed with dichloromethane. The filtrate was concentrated under reduced pressure to obtain a white solid oil suspension. The product 4 was purified by column chromatography on silica using dichloromethane/EtOAc=8/1 ($R_f$=0.29) as eluent to obtain 8.5 g (64%) as a glass.

Synthesis of Fmoc-Lys(Boc)-Lac-OH 5

Fmoc-Lys(Boc)-Lac-OBn 4 (6.11 g, 9.69 mmol) was dissolved in 95% ethanol (200 mL) and the solution was purged with Ar for 10 min. To this solution 10% Pd/C (0.367 g) was added and the mixture was stirred under H$_2$ atmosphere at room temperature. After 1 h, the resulting mixture was filtered through "Celite" (Trademark, Celite Corp.) and the filter cake was washed with dichloromethane. The filtrate was concentrated under reduced pressure. The product was purified by column chromatography on silica using EtOAc/hexane=2/1 as eluent to obtain 3.506 g (65%) of desired product as a white solid.

[Lys-Lac] monomer 5 can be employed in solid phase peptide synthesis to prepare [Lys-Lac] oligomers. Solid phase peptide synthesis (SPPS) is a well-known method to prepare peptides. See: D. Richwood and B. D. Hames (1989), "Solid Phase Peptide Synthesis, A Practical Approach," IRL Press; Erickson, B. W. and Merrifield, R. B. (1976) "Solid-phase synthesis," in *The Proteins* (Eds,. H. Neurath and R. L. Hill) Vol.2, 3rd Ed., p. 255–257. Academic Press, New York.

Standard SPPS methods are employed in the synthesis of polycationic oligomers of Formula IIA–C except that the coupling reaction time was extended from the standard 20 min to about 2 h to provide good coupling yields and the standard deprotection reaction times extended by about 50%. It is believed that these modifications are needed in the preparation of the repeating structures of the polycationic oligomers of this invention because of secondary structure formation during synthesis. SPPS methods are believed to be most applicable to synthesis of oligomers where n is 50 or less. It was also found that when difficult couplings were encountered, typically during the later stages of the synthesis of an oligomer by SPPS methods, successfully coupling could be achieved by use of excess protected amino acid (or protected monomer) and repeating acylations until a>99% yield was achieved. A double-deprotection step was also found to improve yields. See Example 7 for details of the solid phase synthesis using protected amino acids as applied to H-[Lys-Ala]$_{28}$-OH.

Synthesis of H-Lys($^t$Boc)-Lac-OBn 6

Piperidine (1.5 mL) was added to a solution of Fmoc-Lys ($^t$Boc-)-Lac-OBn 4 (2.2175 g, 3.51 mmol) in DMF (60 mL) at room temperature and the solution was stirred for 1 h. The reaction was quenched with 3N HCl (1 mL). DMF was then removed under vacuum. The residue oil was taken up with water and extracted with dichloromethane. The combined organic layer was dried over Na$_2$SO$_4$, filtered and concentrated to obtain a light yellow solid. The components of the solid were crudely separated by packing the solid on silica and first washing with EtOAc/hexane=2/1, then flushing the desired product 6 off the column with methanol to obtain 0.7338 g of 6 a light yellow oil. The material was used without further purification.

Synthesis of Fmoc-Lys($^t$Boc)-Lac-Lys(Boc)-Lac-OBn 7

A solution of Fmoc-Lys($^t$Boc)-Lac-OH 5 (0.9415 g, 1.74 mmol), H-Lys($^t$Boc)-Lac-OBn 6 (0.733 g, 1.79 mmol), 1-hydroxybenzotriazole hydrate (HOBt, 0.2484 g, 1.84 mmol) and DCC (0.418 g, 2.03 mmol) in dichloromethane (80 mL) was stirred at room temperature overnight. The resulting yellow cloudy solution was evaporated to dryness and purified by column chromatography on silica using EtOAc/hexane=1/1 ($R_f$=0.5) as eluent to obtain 1.0218 g (63%) of 7 as a white solid.

Synthesis of Fmoc-Lys-Lac-Lys-Lac-OBn 8

Trifluoroacetic acid (TFA, 0.2 mL, excess) was added to a solution of Fmoc-Lys($^t$Boc)-Lac-Lys($^t$Boc)-Lac-OBn 7 (0.1 g, 0.107 mmol) in dichloromethane (10 mL) at room temperature. The resulting light yellow solution was stirred at room temperature overnight. The reaction was quenched with saturated NaHCO$_3$, extracted with dichloromethane, dried over Na$_2$SO$_4$, filtered, and then dried under vacuum to obtain the $^t$Boc deprotected dimer 8.

Example 2

Synthesis of H-[Lac-Lys]$_n$-OH by reference to Scheme 2

Synthesis of 2-(S)-t-butyldiphenylsiloxy propanoic acid 10

A solution of t-butylchlorodiphenylsilane, TBDPSCl, (7.9 g, 28.9 mmoL) in THF (20 mL) was slowly added via canula into a solution of triethylamine (7.4 mL, 53.1 mmol), DMAP(catalytic amount) and L-(+)-lactic acid 9 (2.0954 g, 26.16 mmol) in THF (20 mL) and dichloromethane (20 mL) at room temperature. The resulting mixture, a white suspension, was stirred at room temperature for 2 days. The reaction mixture was washed sequentially with water, 3N HCl and water, dried over Na$_2$SO$_4$, filtered and solvent was removed under vacuum. The product was purified by column chromatography on silica using EtOAc/hexane=1/3 and 1/1 as eluent to obtain 4.965 g (58%) of 10.

Synthesis of TBDPS-Lac-Lys(Cbz)-OMe 12

A solution of 2-(S)-t-butyldiphenylsiloxy propanoic acid 10 (3.6977 g, 11.26 mmol), 1-ethyl-3-(3-dimethylaminopropyl) carbodiimide•HCl (EDAC, 2.1692 g, 11.32 mmol), Nε-Cbz-L-lysine methyl ester•HCl 11 (3.6721 g, 11.1 mmol), triethylamine (1.6 mL, 11.48 mmol) and HOBt (1.5316 g, 11.33 mmol) in dichloromethane (~250 mL) was stirred at room temperature for 36 h. The reaction mixture was taken up with water and extracted with dichloromethane. The combined organic layers were washed with water and brine, dried over Na$_2$SO$_4$, filtered and concentrated under reduced pressure to obtain a clear oil. The product was purified by column chromatography on silica using EtOAc/hexane=1/2 ($R_f$=0.25) as eluent to obtain 6.2094 g (93%) of desired product 12 as a glass.

Synthesis of TBDPS-Lac-Lys(Cbz)-OH 13

A mixture of TBDPS-Lac-Lys(Cbz)-OMe 12 (0.192 g, 0.317 mmol) and LiOH (55.3 mg, 2.31 mmol) in methanol/ water (7:3, 20 mL) was stirred at room temperature for 3 h. The reaction mixture was acidified with 3N HCl. Methanol was then removed under reduced pressure. The resulting residue was taken up with water (~50/mL) and dichloromethane (~50 mL). The organic layer was separated and washed with water, dried over $Na_2SO_4$, filtered, concentrated then dried under vacuum to obtain the product 13 as a glass (0.17 g, 91%). This product was used without further purification.

[Lac-Lys] monomer 13 can be employed in solid phase peptide synthesis to produce [Lac-Lys] oligomers.

Example 3

Synthesis of H-[Lys-Ala]$_n$—OH by reference to Scheme 3

Synthesis of $^t$Boc-Lys(Cbz)-Ala-OMe 16

Nα-t-Boc-Nε-Cbz-L-lysine 14 (6.2 g, 16.3 mmol), L-alanine methyl ester•HCl 15 (2.2735 g, 16.3 mmol), triethylamine (2.3 mL, 16.5 mmol), HOBt (6.224 g, 16.46 mmol), EDAC (3.1877 g, 16.63 mol) and DMAP (catalytic amount) in dichloromethane (80 mL) was stirred at room temperature overnight. The reaction was diluted with dichloromethane (~100 mL) then washed with water. The organic layer was dried over $MgSO_4$, filtered and concentrated under reduced pressure to obtain a light yellow oil. The product was purified by column chromatography on silica using EtOAc/hexane=1/1 ($R_f$=0.18) as eluent to obtain 6.4545 g (85%) of desired product 16 as a clear glass.

Synthesis of $^t$Boc-Lys(Cbz)-Ala-OH 17

A mixture of $^t$Boc-Lys(Cbz)-Ala-OMe (6.4545 g, 13.86 mmol) 16 and LiOH (1.004 g, 41.8 mmol) in methanol/water (80/10 mL) was stirred at room temperature for 4 h. The reaction mixture was neutralized with 0.5 N citric acid and methanol was removed under reduced pressure. The resulting aqueous solution was diluted with water and extracted with dichloromethane and ethyl acetate. The combined organic layer was washed with brine, dried over $MgSO_4$, filtered, concentrated and dried under vacuum to obtain 17 as a white solid (3.445 g, 55%). The product was used without further purification.

Monomer 17 can be employed in solid phase peptide synthesis to produce the [Lys-Ala] oligomers.

Example 4

Methods for preparing monomers with tethered groups are exemplified with a DHT tether to glutamic acid by reference to Scheme 4.

A mixture of N-Cbz-L-glutamic acid 20 (4.067 g, 14.46 mol), paraformaldehyde (0.889 g, 29.63 mmol) and p-toluenesulfonic acid monohydrate (TsOH•$H_2O$, 0.163 g, 0.86 mmol) in benzene (100 mL) was heated to reflux for 2 h, with removal of water in a Dean-Stark trap. The reaction was cooled to room temperature and diluted with ethyl acetate (~50 mL). The product was extracted with 5% aqueous $K_2CO_3$ (~50 mL). The aqueous layer was separated and neutralized with 3N HCl, then extracted with ethyl acetate. The organic layer was dried over $MgSO_4$, filtered, concentrated under reduced pressure and dried under vacuum. The product, N-Cbz-glutamic acid oxazolidinone, 21 (3.7044 g, 87%) was used without further purification.

Route A to Glutamic Acid Tether $BH_3$•$SMe_2$ (0.33 mL, 3.3 mmol) was added to a solution of N-Cbz-glutamic acid oxazolidinone 21 (0.65 g, 2.21 mmol) in THF (10 mL) at room temperature and the mixture was stirred for 4 h. The reaction was quenched with methanol (2 mL) and stirred for another 2 h. Solvent was then removed under reduced pressure. The resulting clear oil was taken up with dichloromethane (50 mL) and water (30 mL). The organic layer was separated, dried over $MgSO_4$, filtered, concentrated and dried under vacuum to obtain a clear glass (0.4984 g, 81%). The product, N-Cbz-glutamic acid oxazolidinone alcohol, 22 was used without further purification. ($R_f$=0.14 in EtOAc/hexane: 1/1).

Methanesulfonylchloride (MsCl 0.14 mL, 1.8 mmol) was added to a ice-cooled solution of triethylamine (0.28 mL, 2.0 mmol) and N-Cbz-glutamic acid oxazolidinone alcohol 22 (0.5088 g, 1.82 mmol) in THF (10 mL). The resulting mixture was stirred in an ice-bath for 30 min and was stirred for an additional 2 h at room temperature. The reaction was then quenched with water and THF was removed under reduced pressure. The resulting mixture was taken up with water (20 mL) and dichloromethane (50 mL). The organic layer was separated and washed with 3N HCl (10 mL) and water (20 mL), dried over $MgSO_4$, filtered, concentrated and dried under vacuum to obtain a light yellow oil. The desired product, N-Cbz-glutamic acid oxazolidinone mesylate 23 where X=MsO was purified by column chromatography on silica using EtOAc/hexane=4/3 as eluent to obtain 0.35 g of desired product 23 as a clear oil (54%, $R_f$=0.21 in EtOAc/hexane=1/1).

A solution of 23 where X=MsO (0.7425 g, 2.08 mmol) and LiI (0.39 g, 2.91 mmol) in acetone (20 mL) was stirred at room temperature overnight. The solvent was removed under reduced pressure. The product, N-Cbz-glutamic acid oxazolidinone iodide, 23 where X=I, was purified by column chromatography using EtOAc/hexane=2/3 to obtain 0.736 g (89%) of 23 as light yellow oil ($R_f$=0.25 in EtOAc/hexane=1/3).

Route B to Glutamic Acid Tether

N-Cbz-glutamic acid oxazolidinone 21 (51.4 mg, 0.18 mmol), 3β-amino-DHT (46 mg, 0.16 mmol, see Example 5), triethylamine (0.05 ml, 0.36 mmol), HOBt (27.4 mg, 0.20 mmol) and EDAC (44.6 mg, 0.23 mmol) were combined in a mixture of dichloromethane (10 mL) and THF (10 mL). The mixture was stirred at room temperature for 40 h. The reaction mixture was then diluted with dichloromethane (~30 mL) and washed with water. The organic layer was separated, dried over $MgSO_4$, filtered and concentrated under reduced pressure to obtain a light yellow oil 25 Cbz-Glu(3-amino-DHT)-oxazolidinone. The product was purified on a silica gel column with EtOAc/hexane:3/2 ($R_f$=0.23) as eluent to obtain 62 mg (68%) of 25 as a clear glass. The oxazolidinone 25 is hydrolyzed (D. Shirlin, J-M. Altenburger (1995) Synthesis 1351) using KOH in methanol to give the Cba-Glu(3-amino-DHT)-OH 26 (where Y is N). The derivatized glutamic acid 26 can be converted to the N$_α$Fmoc-protected analog by a known procedure: W-R. Li, J. Jiang and M. M. Joullie (1993) Syn. Lett. 362.

The DHT-tethered glutamic acid 26 can be used directly or coupled with protected lysine to give the protected [Lys-Glu(DHT)] monomer which can be employed in solid phase synthesis to introduce tethered groups into polycationic oligomers.

Example 5

Methods for preparing monomers with tethered groups are further exemplified with a DHT tether to malic acid by reference to Schemes 5A and 5B.

DHT Tether from Malic Acid (A) by reference to Scheme 5A.

A mixture of L-malic acid (16.87 g, 0.126 mmol), 2,2-dimethoxypropane (30 mL, 0.244 mmol) and 4Å molecular sieves (25 g) in toluene (60 mL) was heated at reflux for 2.5 h. The clear solution was cooled to room temperature, filtered through "Celite," (Trademark) and washed with dichloromethane. The solvents were evaporated to dryness under reduced pressure. The residue was purified by recrystallization for ethyl ether and hexane to give the desired product dimethyloxalane 42 (15 g) as a white solid.

3-amino DHT is coupled to the dimethyloxalone 42 as in Route B of Example 4 to give compound 43. The oxalone ring of 43 is opened by a conventional method in base to give the DHT-derivatized malic acid 44.

The DHT tethered malic acid 44 can be coupled with the protected lysine N-tBoc-lys-(N-Cbz)OH to give the protected [Lys-Mal(DHT)] monomer 45.

This monomer 45 can be employed in solid phase synthesis to introduce tethered groups into polycationic oligomers.

DHT-tether from Malic Acid (B) by reference to Scheme 5B

Freshly distilled trifluoroacetic acid anhydride (TFAA, 18 mL) was added to L-malic acid (11.969 g, 89.3 mmol) at room temperature. Within 5 min the solution became homogeneous. After 2 h, TFA and TFAA were removed under reduced pressure. The resulting oil was dissolved in dichloromethane (~30 mL) and benzyl alcohol (10 mL) was added to the solution. The mixture was stirred at room temperature overnight. The reaction mixture was taken up with water and extracted with ethyl acetate. The combined organic layers were washed with water, dried over $Na_2SO_4$, filtered and concentrated under reduced pressure to obtain a clear oil. The product was used without further purification. This method follows a known procedure: M. J. Miller et al. (1982) J. Org. Chem. 47:4928.

1,8-diazabicyclo[5.4.0]undec-7-ene[DBU] (2.4 mL, 16.0 mmol) was added slowly to a solution of 46 (1.336 g, 6.42 mmol) in dichloromethane (20 mL) at room temperature. To the resulting solution, a solution of TBDPSCl (1.7934 g) in dichloromethane (10 mL) was added. The solution was then heated to reflux overnight. The reaction was quenched with 3N HCl, washed with water, dried over $MgSO_4$, filtered, concentrated and dried under vacuum. The product 47 was purified by column chromatography using 3N HCl EtOAc/hexane=2/3 as eluent to obtain the product as a clear glass (1.3145 g).

TBDPS protected benzyl malic ester 47 is derivatized with 3-amino DHT as described in Example 4, route B, to give the protected γ(3-amino-DHT)-malic acid 48.

The TBDPS protecting group on 48 can be removed with $Bu_4NF$. See S. Hanessian and P. Lavallee (1975) Can. J. Chem. 53:2975. The free alcohol can be coupled to a protected lysine as described in Example 1 to give [Lys-Mal(DHT)] monomer for use in SPPS. Alternatively, the benzyl ester can be deprotected using $H_2$, 10% Pd/C. The free acid can then be used in SPPS.

Example 6

Preparation of DHT derivatives

Methods for derivatizing sterols and related compounds in preparation for tethering in polycationic oligomers are exemplified by derivatization of DHT as illustrated in Scheme 6.

3-amino-DHT (A)

A solution of DHT (0.523 g, 1.80 mmol), ammonium acetate (1.45 g, 18.8 mmol) and sodium cyanoborohydride (0.145 g, 2.3 mmol) in MeOH (30 mL) was stirred at room temperature overnight (~16 h). The reaction was quenched with 1 N NaOH (20 mL) and stirred for 30 min. The resulting mixture was taken up with water and extracted with dichloromethane. The combined organic layer was washed with brine, dried over $MgSO_4$, filtered, concentrated and dried under vacuum to obtain a white solid. $^1$H-NMR of the crude material showed the desired product 50 with the ratio of α/β-amino substitution=1/1.8. The crude product was purified by column chromatography using methanol/dichloromethane (2/1) and MeOH as eluent, collecting 50 mL fractions. The diastereomers cannot be distinguished by TLC. $^1$H-NMR showed the 3rd fraction from the column contained α-amino-DHT along with some impurities. The 4th fraction (52 mg) contained α-amino-DHT. The 5th and 6th fractions (100.8 mg) contained both α and β-amino-DHT (~1/1). The 7th to 10th fractions (93.6 mg) contained β-amino DHT and a relatively small amount of α-amino-DHT. The 11th fraction (46 mg) contained β-amino-DHT. The total yield of 3-amino-DHT 50 was 56%.

3-amino-DHT (B)

A solution of DHT (1.0814 g, 3.72 mmol) and benzylamine (0.55 ml, 4.58 mmol) in dichloromethane (20 mL) was stirred at room temperature for 1 h. Sodium cyanoborohydride (0.51 g, 8.1 mmol) was added to the solution and the resulting mixture was stirred at room temperature for 4 days. The reaction was quenched with 1 N NaOH (2 mL) stirred for 10 min. followed by addition of saturated aqueous $NaHCO_3$ (30 mL) and stirred an additional 30 min. The resulting white suspension was filtered to collect a white solid which was washed with water and ether. The white solid was dried under vacuum to obtain the product 3-benzylamino-DHT, 51, (0.69 g). The white solid was found to be β-benzylamino DHT by $^1$H-NMR. The solid was purified by extraction with dichloromethane. The organic layer of the filtrate was separated, washed with brine, dried over $MgSO_4$, filtered, concentrated and dried under vacuum. The dried solid from the filtrate was then further purified by elution from a silica column using EtOAc/hexane 2/1 as the eluent. The total yield of β-benzyl amino-DHT was 0.7984 g (56%).

The 3-benzylamino-DHT can be converted to the 3-amino-DHT by reduction using $H_2$ with 10% Pd/C catalyst.

3-(3-amino-1-propanol)-DHT

A solution of DHT (0.2885 g, 0.99 mmol) and 3-amino-1-propanol (0.11 mL, 1.44 mmol) in dichloromethane (5 mL) was added to a slurry of sodium triacetoxyborohydride (0.3985 g, 1.88 mmol) in anhydrous dichloromethane (10 mL). The mixture was stirred at room temperature for 2.5 days. The reaction was quenched with 1 N NaOH (2 mL) and stirred for 10 min. The resulting mixture was taken up with water and extracted with dichloromethane. The combined organic layer was washed with saturated $NaHCO_3$ water and brine, dried over $MgSO_4$, filtered, concentrated and dried under vacuum to obtain a white solid. $^1$H-NMR of the crude product indicates the product 52 with a diastereomer (3β:3α) ratio of about 1:5. The mixture of 3β- and 3α-diastereomers was separated by packing on a short path silica gel column with dichloromethane and washing with EtOAc (~50 mL), EtOAc/MeOH=1/1 (~250 mL) and MeOH (~100 mL), collecting 50 mL fractions. The diastereomers could not be distinguished by TLC. NMR analysis shows fraction 2–6 contain the 3α-amino-DHT (0.1447 g, 48%).

The 3-(3-amino-1-propanol)-DHT can be used in peptoid synthesis as discussed above after functional group transformation to introduce tethered groups into peptoid polycationic oligomers.

Example 7

Solid Phase Synthesis of H-[Lys-Ala]-OH employing protected amino acids

Alternating polycationic peptides of this invention can be prepared by stepwise addition of protected amino acids using SPPS methods.

(a) Trifluoroacetate salt of H-(Lys-Ala)28-OH

This peptide was assembled at a 0.1 mmol scale on a Fmoc-Ala Wang resin (0.45 mmol/g) using standard Fmoc solid phase peptide synthesis (Field, G. B. and Noble, R. L. (1990) Int. J. Peptide Protein Res. 35:161–214). The acylations were performed using a ten-fold molar excess of HOBt esters of Fmoc-Ala or Fmoc-Lys(Boc) in either DMF or NMP (30 min–60 min at 25° C.). When "difficult" couplings were encountered (i.e., during later stages of synthesis), acylations were repeated using an additional ten-fold molar excess of Fmoc-amino acids until a >99% yield was achieved as determined by quantitative ninhydrin assay and solid-phase Edman sequencing (Pohl, J. (1994) Methods Mol. Biol. 36: 107–129). The deprotection of Fmoc group was affected by 20% (v/v) piperidine in NMP (20 min at 25° C.). In later stages of synthesis (e.g., past about residue 30), a double-deprotection protocol was used in order to achieve >99% deprotection yields. The peptide was cleaved off the resin and deprotected using TFA/anisole (9:1, v/v, 10 ml/g resin, 2 h at 25° C.). The crude peptide was obtained by precipitation with cold diethyl ether. The peptide was purified by reversed-phase HPLC on a Zorbax SBC18 silica column (22×250 mm) equilibrated in 0.1% aqueous TFA and eluted using a linear gradient of acetonitrile (0.5%/min) in 0.08% aqueous TFA. The fractions containing the desired product were lyophilized. The purified peptide TFA salt (56 mg, 10% yield) yielded a single peak on analytical reversed-phase HPLC; its amino acid composition [Ala(1.00), Lys (0.95)] and its mass (m/z=5,597 amu) are in agreement with the expected values.

The following polycationic oligomer is an example of a polycationic oligomer of structure IV with regions of alternating cationic groups separated by flexible spacer groups.

(b) Trifluoroacetate salt of H-(Lys-Ala)5-eACA-(Lys-Ala)5-OH

This peptide (where eACA is 6-aminohexanoyl) was assembled at a 0.5 mmol scale on a Boc-Ala PAM-resin (0.7 mmol/g) using standard Boc/benzyl solid phase synthesis (Field, G. B. and Noble, R. L. (1990) supra). The acylations were performed using a four-fold molar excess of HOBt esters of Boc-Ala or Boc-Lys(Cl-Z) in NMP (60 min at 25° C.). The deprotection of the Boc group was affected by 55% (v/v) TFA in DCM (20 min), and the neutralization of the resin was affected by DIEA in NMP. The peptide was cleaved off the resin and deprotected in liquid HF/anisole (9:1, v/v, 60 min at 0 deg C.); it was extracted into 30% (v/v) aqueous acetic acid and lyophilized. The peptide was purified by reversed-phase HPLC on a Zorbax SBC18 silica column (22×250 mm) equilibrated in 0.1% aqueous TFA and eluted using a linear gradient of acetonitrile (0.5%/min) in 0.08% aqueous TFA. The fractions containing the desired product were lyophilized. The purified peptide TFA salt (310 mg, 30% yield) yielded a single peak on analytical reversed phase HPLC; its amino acid composition [Ala(1.00),Lys (0.98), eACA(0.09)] and its mass (m/z=2,124 amu) are in agreement with the expected values.

(c) Trifluoroacetate salt of H-Cys(NPYS)-(Lys-bAla)19-Lys-Ala-OH

This peptide (where bAla is 3-aminopropionyl and NPYS is 3-nitro-2-pyridinesulphenyl) was prepared on a 0.01 mmol scale using the Boc/benzyl protection strategy as described in Example 7b. The purified peptide TFA salt (14 mg, 30% yield) yielded a single peak on analytical reversed-phase HPLC; its amino acid composition [Ala(1.00), Lys (19.1), bAla(19.5), Cys was not quantified] and its mass (m/z=4,661 amu) are in agreement with the expected values.

Example 8

Mobility Shift DNA-Binding Assays

Protein-DNA binding interactions have been assessed in the art using mobility shift assays. See, F. M. Ausubel et al. (eds.) Current Protocols in Molecular Biology (1996), John Wiley and Sons, Inc., p.12.2.1–12.2.10. Typically, the method employs polyacrylamide gel electrophoresis in which protein-DNA complexes are retarded compared to non-complexed DNA. A variation of the standard mobility shift assay has been employed herein using agarose gel electrophoresis to assess polycationic oligomer binding to oligonucleotides and charge neutralization of the oligonucleotide.

A 28 base oligonucleotide of sequence:

GGGAGGAGGAGGTGGAGGAGGAAGAGGA (SEQ. ID NO. 1)

was synthesized by standard automated procedures. This oligonucleotide is the triplex-forming antisense oligonucleotide, HN28ap PDE (phosphodiester), which binds the her-2/neu promoter and shuts down transcription in cells. S. W. Ebbinghaus et al.(1993) J. Clinical Investigation 92:2433–2439. The phosphorothioate analogue, designated HN28ap PTE (phosphorothioate ester), of the 28-mer HER-2/neu was also prepared by known methods. See: S. Agrawal, (ed.), (1993) Methods in Molecular Biology, Vol. 20: "Protocols for Oligonucleotides and Analogues," Humana Press, Inc. Totowa, N.J., including pages 33–61.

[Lys-Ala]$_n$ sequential oligomers with n=12, 24 and 28 were synthesized by methods described herein.

The oligonucleotide or its phosphorothioate analogue were end-labelled with [γ32P]-ATP using T4 polynucleotide kinase, diluted, mixed with an equal volume of oligomer or poly(L-lysine)[PLL] in either phosphate buffered saline (PBS) or (TMS) (20 mM Tris (pH 8.0), 40 mM MgCl$_2$, 30% sucrose) buffer at 37° C. and allowed to incubate for 30 minutes. The labelled oligonucleotide was mixed with varying amounts of [Lys-Ala]$_n$ oligomers or PLL [Product No.P2636, Lot number 4H-5537, Sigma, St. Louis, Mo., Mol. Wt. 53,900 (viscosity) 54,300 (laser angle long light scattering, LALLS)]. This PLL has approximately 259 lysines/molecule. The labelled 28-mer was mixed with equimolar, 10- or 100-fold molar excess of [Lys-Ala]$_{12}$ (SEQ ID NO: 4), [Lys-Ala]$_{24}$ (SEQ ID NO: 5), [Lys-Ala]$_{28}$ (SEQ ID NO:6), or PLL. The concentration of oligomer and PLL added in each case was determined by amino acid compositional analysis.

The incubated oligonucleotide-polycationic oligomer mixtures in the two different incubation buffers were subjected to agarose gel (2%) electrophoresis (tris-borate-EDTA buffer pH 7.0) in a horizontal gel electrophoresis apparatus with an applied voltage of 0.75 v/cm to assess mobility shift. In this assay, fully complexed charge neutralized oligonucleotides would be predicted to display little or no migration in the gel. Autoradiographs of gels indicate that [Lys-Ala]$_{28}$ (SEQ ID NO: 6) at equimolar, 10- and 100-fold molar excess results in significant inhibition of mobility of the 28-mer HN28ap oligonucleotide. In contrast, [Lys-Ala]$_{12}$ (SEQ ID NO: 4) even at 100-fold molar excess had minimal effect on mobility of the 28-mer. [Lys-Ala]$_{24}$ (SEQ ID NO: 5), which is about 14% (4/28) mismatched in size to the 28-mer oligonucleotide compared to [Lys-Ala]$_{28}$ (SEQ ID NO: 6), shows significant inhibition of mobility of the 28-mer when combined at 10- and 100-fold molar excess. Visual inspection of autoradiograms indicates that [Lys-Ala]$_{24}$ (SEQ ID NO: 5) is somewhat less effective than [Lys-Ala]$_{28}$ (SEQ ID NO: 6). At all levels assayed PLL significantly inhibited mobility of the 28-mer in the agarose gel.

No significant difference in mobility shift results was noted when different incubation buffers (PBS or Tris-magnesium sucrose) were used.

Mobility assays performed under analogous conditions on 2% agarose gels with the phosphorothioate analogue HN28ap DTE complexed to [Lys-Ala]$_{12}$ (SEQ ID NO: 4), [Lys-Ala]$_{24}$ (SEQ ID NO: 5), [Lys-Ala]$_{28}$ (SEQ ID NO: 6) or PLL (equimolar, 10- or 100-fold molar excess) gave similar mobility results.

An analogous gel-shift assay was performed to assess the effect of application of an annealing cycle during HN28ap/[Lys-Ala]$_{28}$ (SEQ ID NO: 6) complex formation. Samples of mixtures of HN28ap/[Lys-Ala]$_{28}$ incubated together for 1 h at 37° C. or subjected to an annealing step. To anneal the mixture is heated to 95° C. for 5 min, after which the mixture is slowly cooled, e.g., 1° C./min., to room temperature. Samples also contained varying ratios of polycationic oligomer to HN28ap (0.5:1 to 100:1). When the carrier is present at less than 1:1 ratio all radiolabelled oligonucleotide was observed to migrate in the electric field indicating net negative charge. At a 1:1 ratio the failure to migrate out of the well is observed, with a slightly greater effect (slightly greater charge neutralization) observed in samples that were pretreated with an annealing cycle. At 10 and 100 fold excess of polycationic oligomer complete charge neutralization is observed.

Example 9

Polycationic Oligomer-Mediated Oligonucleotide Introduction into Cells

In general, the oligonucleotide-polycationic oligomer mixture is incubated with eukaryotic cells, such as human cancer cells, in standard tissue culture medium at physiologic conditions. Cell are grown using standard well-known methods compatible with transfection. After incubation, the cells are rinsed with Dulbecco's phosphate buffered saline to remove labelled oligonucleotides that have not been taken up into cells and uptake of oligonucleotides is assessed by scintillation counting of the washed cell pellet. Polycationic oligomer-mediated uptake of nucleic acid can be compared to uptake by cells incubated with nucleic acid alone. Positive controls can include carrier-independent methods of introducing nucleic acid into cells, e.g., electroporation or Ca-phosphate-mediated introduction.

More specifically, the appropriate cell line is harvested by trypsinization, resuspended and counted on a hemocytomer. Concentration is adjusted, typically to 10$^6$ viable cells/ml medium and aliquots of cells (typically 200 µL/2×10$^5$ cells) are placed in Eppendorf tubes and mixed with oligonucleotide, oligonucleotide:carrier complex and any other appropriate control treatments. The cells and treatment are incubated at 37° C. for from about 1 h to about 4 h. Following incubation, 1 ml PBS is added to each tube, vortexed and centrifuged at 4700 rpm (2000×g) for 40 s in a microcentrifuge. Supernatant is decanted and cells are washed with two additional aliquots of PBS. The final wash is aspirated, and the cell pellet is counted in liquid scintillation fluid.

Aliquots of the oligonucleotide-polycationic oligomer and oligonucleotide-PLL mixtures of Example 8 were incubated with LNCaP.FGC metastatic prostate adenocarcinoma cells (American Type Culture Collection ATCC CRL-1740, Passage Frozen: 20, grown in RPMI 1640 supplemented with 10% (by volume) fetal bovine serum (FBS) and Pen/Strep antibiotics) for 1 h at 37° C. Cells were grown using standard well-known methods compatible with transfection. After incubation, the cells were rinsed with PBS several times to remove labelled oligonucleotides that had not been taken up into cells. Cells were pelleted and uptake of oligonucleotides was assessed by scintillation counting.

In this experiment, cellular uptake of the 28-mer radiolabeled oligonucleotide was greatest when it was complexed with [Lys-Ala]$_{28}$ (SEQ ID NO: 6) or PLL. Cellular uptake of the radiolabeled 28-mer complexed to [Lys-Ala]$_n$ generally increased in the order [Lys-Ala]$_{12}$ (SEQ ID NO: 4)< [Lys-Ala]$_{24}$ (SEQ ID NO: 5)<[Lys-Ala]$_{28}$ (SEQ ID NO: 6), with uptake with [Lys-Ala]$_{28}$ significantly greater than uptake with [Lys-Ala]$_{12}$. Similar results were observed for uptake of the radiolabeled 28-mer phosphorothioate analogue. No significant difference in uptake results was noted when different incubation buffers (PBS or Tris-magnesium sucrose) were used.

A separate uptake experiment was performed to assess the effect of use of an annealing cycle during oligonucleotide-polycationic oligomer complexation on later nucleic acid uptake by cells contacted with the complex. Uptake of radiolabel was measured in LNCaP cells with HN28ap complexed with [Lys-Ala]$_{28}$ (SEQ ID NO: 6). A 2 or 4 h incubation period with HN28ap/[Lys-Ala]$_{28}$ (SEQ ID NO: 6) complex (+/−annealing) and with varying relative amounts of polycationic oligomer to HN28ap (HN28ap alone, ratios of 0.5:1 to 100:1 of oligomer to HN28ap) were assessed. Little or no uptake is observed in the absence of the oligomer carrier. Uptake in presence of the oligomer increases generally with increased molar ratio of oligomer to nucleic acid. Uptake also generally increases with increasing incubation time from 2 to 4 h. Uptake also generally increases with application of an annealing step during complex formation.

Cellular uptake of HN28ap was found to generally correlate with charge neutralization of the complex assessed by electrophoretic gel-shift assays.

Example 10

Effect of HN28ap transfection on expression of HER-2/neu in prostate cancer cell lines In this example, Western blot analysis coupled with densitometric quantification of band intensities is used to quantify HER-2/NEU protein expression in a whole protein extract of cultured cells.

Western analysis of protein extracts of three prostate cancer cell lines, LNCaP, PC-3 and DU-145, is performed. A breast cancer cell line, SKBR-3, known to overexpress HER-2/NEU was also analyzed as a positive control. The relative expression level of HER-2/NEU protein when equal amounts of total protein are assayed are SKBR- 3>DU145>PC-3>LNCaP. The androgen receptor was shown to be expressed only in the LNCAP cell line, as expected. Similar levels of actin expression were observed indicating equal loading.

Figure 3:
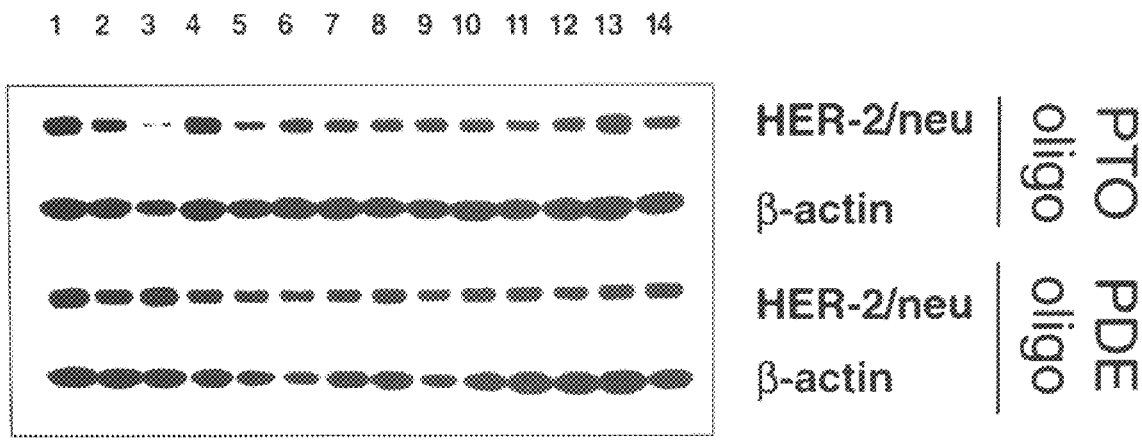
FIG. 3 is a western blot measuring HER-2/NEU expression in LNCaP cells transfected with HN28ap as the phosphodiester (PDE, blot b)) or as the phosphorothioate ester (PTE, blot a) using varying concentrations of $[Lys-Ala]_{28}$ and high molecular weight PLL as carriers. See: Example 10.

The effect of HN28ap either the phosphodiester (PDE) or the corresponding phosphorothioate ester (PTE) on HER-2/NEU protein expression in LNCaP cells was examined by western blot analysis. LNCaP cells were transfected with PTE HN28ap or PDE HN28ap using [Lys-Ala]$_{28}$ (SEQ ID NO: 6) or HMWPLL (high molecular weight poly-L-lysine). The treatments associated with lanes 1–14 of FIG. 3 are as follows:

| Lane | Lys-Ala$_{28}$(SEQ ID NO:6) ($\mu$M) | HMWPLL ($\mu$M) | HN28ap ($\mu$M) |
|---|---|---|---|
| 1 | 100 | — | 10 |
| 2 | 10 | — | 10 |
| 3 | 10 | — | 1 |
| 4 | — | 1 | 10 |
| 5 | — | 1 | 5 |
| 6 | — | 0.1 | 1 |
| 7 | — | — | 10 |
| 8 | — | — | 5 |
| 9 | — | — | 1 |
| 10 | 100 | — | — |
| 11 | 10 | — | — |
| 12 | — | 1 | — |
| 13 | — | 0.1 | — |
| 14 | — | — | — |

In each case duplicate wells containing 2×10 of LNCAP cells were treated with media containing carrier/oligo combinations as indicated in the Table and incubated for 24 hours.

It was found that only the phosphorothioate oligonucleotide (Blot A) was effective in inhibiting HER-2/NEU protein expression in LNCaP cells when introduced into cells with (KA)$_{28}$ or HMWPLL.

When 1 $\mu$M PTE of HN28ap was complexed with either 10 $\mu$M [Lys-Ala]$_{28}$ (SEQ ID NO: 6) or 0.1 $\mu$M HMWPLL, significant decreases in HER-2/NEU protein levels were seen. No effect on protein levels was observed when the oligonucleotide was applied at 1 $\mu$M, 5 $\mu$M or 10 $\mu$M. [Lys-Ala]$_{28}$ and HMWPLL alone at similar concentrations had no effect on expression. Higher concentration of oligonucleotide (5–10-fold over 1 $\mu$M) were less effective at inhibiting HER-2/neu protein expression even when the ratio of carrier:oligonucleotide was kept constant. Densiometric scanning (corrected for relative intensity of actin) shows that HER-2/NEU intensity in lane 3 ([Lys-Ala]$_{28}$:DTE HN28ap) is only 28% of lane 9 (DTE HN28ap) and 43% of lane 14 (media alone). This represents a 2.3 fold to 3.6 fold decrease in protein expression from HN28ap delivered by [Lys-Ala]$_{28}$. Also, actin-normalized band intensity in lane 6 (HMWPLL:HN28ap) is only 62% of lane 8 (oligo alone, same concentration), and 94% of lane 14 (media alone). Thus, when corrected for differences in protein loading, HMWPLL is significantly less effective as a carrier of HN28ap than [Lys-Ala]$_{28}$.

Those of ordinary skill in the art will appreciate that methods, procedures, techniques, reagents and conditions specifically described herein can be modified or routinely adapted without departing from the objectives of this invention. All such modifications and adaptations and functional equivalents of the specifically disclosed embodiment are intended to be encompassed with the spirit and scope of this invention.

All references cited herein are incorporated in their entirety by reference herein.

We claim:

1. A transfection composition which comprises a nucleic acid or a salt thereof and a polycationic oligomer or a salt thereof having the repeating structure:

where M is an optional flexible spacer, r1 and r2, independently, are 1 or 0 to indicate the presence or absence of a given M; REP is a repeating unit containing a cationic side group; m1, m2, and m3 are integers indicating the number of repeating units and l is an integer indicating the number of repetitions of

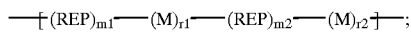

wherein the total number of repeating units in the polycationic oligomer n is equal to l(m1+m2)+m3, wherein REP is a repeating unit having the structure:

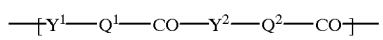

wherein $Y^1$ is O or $NR^3$ and $Y^2$ is O or $NR^4$ and one of $Q^1$ or $Q^2$ in a repeating unit is —$(CH_2)_w$—, where w is an integer ranging from 1 to 3 and the other of $Q^1$ or $Q^2$ in a repeating unit is —CH(R')—; and R', $R^3$ and $R^4$ can be H, a lower alkyl having from 1–3 carbon atoms, a non-cationic side group or a cationic side group with the proviso that there is one and only one cationic side group in each repeating unit and wherein n is selected such that the polycationic oligomer is comparable in length to said nucleic acid.

2. The transfection composition of claim 1 wherein M is:

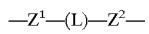

where $Z^1$ and $Z^2$, independently of one another, are chemical groups that can form a covalent bond between repeating units and L is a flexible length spacer that is an alkyl group, an ether group or a thioether group.

3. The transfection composition of claim 2 wherein $Z^1$ and $Z^2$, independently, are NR, where R is hydrogen or a lower alkyl having 1 to 3 carbon atoms, —CO—, O or —S—.

4. The transfection composition of claim 3 wherein one of $Z^1$ or $Z^2$ is NH and the other of $Z^1$ or $Z^2$ is CO and L is —$(CH_2)_q$— where q is an integer ranging from 2 to 10, inclusive.

5. The transfection composition of claim 1 wherein r1 and r2 are both 0.

6. The transfection composition of claim 1 wherein REP is a repeating unit having the structure:

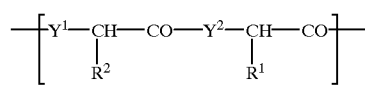

where each $Y^1$, independently of $Y^1$ in other repeating units, can be O or $NR^3$; each $Y^2$, independently of $Y^2$ in other repeating units, can be O or $NR^4$; and one of $R^1$ or $R^2$ or one of $R^3$ or $R^4$ in each repeating unit is a cationic group and the other of $R^1$ or $R^2$, or $R^3$ or $R^4$ in a repeating unit, is a non-cationic group selected from the groups consisting of a hydrogen, an alkyl group, an unsaturated alkyl group, an aryl group, a tether group or a tethered group and wherein n is selected such that the polycationic oligomer is comparable in length to said nucleic acid.

7. The transfection composition of claim 6 wherein r1 or r2 is 1 and M is a group having the structure:

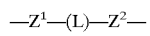

where $Z^1$ and $Z^2$, independently of one another, are NR with R being hydrogen or a lower alkyl having 1 to 3 carbon atoms, —CO—, O or —S— and L is an alkyl group, —$(CH_2)_q$— where q is an integer that preferably ranges from 2 to about 10 in which one or more non neighboring —$CH_2$— groups can be replaced with an oxygen or a sulfur.

8. The transfection composition of claim 7 wherein q is an integer ranging from 3 to 8.

9. The transfection composition of claim 7 wherein $Z^1$ and $Z^2$ are NH and CO.

10. The transfection composition of claim 6 wherein m1, m2 and m3 are integers having values of 3–6.

11. The transfection composition of claim 6 wherein m1 and m2 are both 5.

12. The transfection composition of claim 6 wherein r1 and r2 are 0 and wherein REP is the repeating unit:

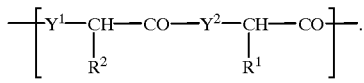

13. The transfection composition of claim 6 the polycationic oligomer has the repeating unit:

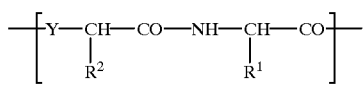

where Y is O or NH.

14. The transfection composition of claim 13 wherein r1 and r2 are 0.

15. The transfection composition of claim 6 wherein the polycationic oligomer has the formula:

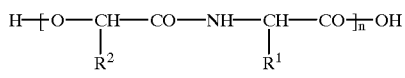

or

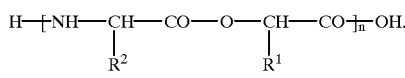

16. The transfection composition of claim 6 wherein the polycationic oligomer has the formula:

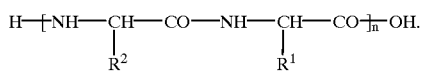

17. The transfection composition of claim 6 wherein the polycationic oligomer has the formula:

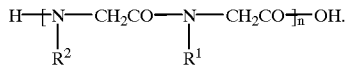

18. The transfection composition of claim 1 wherein said cationic side groups are selected from the group $-(CH_2)_t X$ where t is an integer from 1 to about 6 and X is an $NH_3^+$ or an $-NH-C(NH_2)=NH_2^+$ group.

19. The transfection composition of claim 18 wherein t is 3 or 4.

20. The transfection composition of claim 19 wherein said cationic side group is $-(CH_2)_4-NH_3^+$ or $-(CH_2)_3-NH-C(NH_2)=NH_2^+$.

21. The transfection composition of claim 1 wherein said non-cationic side groups are selected from the group consisting of a hydrogen, an alkyl group having from 1 to about 6 carbon atoms, a $-(CH_2)_s-WR^5$ group where s is an integer from 1 to about 6; W is an O atom, S atom or a COO, NH, NHCO or CONH group; $R^5$ is a hydrogen or alkyl group having from 1 to 6 carbon atoms.

22. The transfection composition of claim 1 wherein said non-cationic side groups are selected from the group consisting of a $-(CH_2)_s-WR^6$ group where s is an integer from 1 to about 6; W is an O atom, S atom or a COO, NH, NHCO or CONH group; $R^6$ is a tethered group selected from the group consisting of:

(i) a ligand for a cell receptor;
(ii) a lipid moiety;
(iii) a hormone peptide;
(iv) a fluorescent label; or
(v) a radiolabel; or
(vi) a combination of groups (i)–(v), wherein
each of (i) to (v) can be first appropriately derivatized to facilitate covalent binding to the tether linking group W.

23. The transfection composition of claim 22 wherein said tethered group is a cell-receptor ligand.

24. The transfection composition of claim 1 wherein said non-cationic side group is a tethered group selected from the group: a ligand for a cell receptor; a lipid moiety; a hormone peptide; a fluorescent label; and a radiolabel.

25. The transfection composition of claim 1 wherein said non-cationic side group is an alkyl or alkoxy group having from 1 to about 6 carbon atoms.

26. The transfection composition of claim 1 wherein said polycationic oligomer is the alternating oligomer [Lys-Ala]n.

27. The transfection composition of claim 1 wherein said nucleic acid is an antisense, antigene or triplex-forming oligonucleotide.

28. The transfection composition of claim 1 wherein said nucleic acid is a ribonucleotide.

29. A charge neutralized complex of a nucleic acid with a polycationic oligomer or a salt thereof of substantially discrete length and having the repeating structure:

where M is an optional flexible spacer, r1 and r2, independently, are 1 or 0 to indicate the presence or absence of a given M; REP is a repeating unit containing a cationic side group; m1, m2, and m3 are integers indicating the number of repeating units and 1 is an integer indicating the number of repetitions of

wherein the total number of repeating units in the polycationic oligomer n is equal to 1(m1+m2)+m3, wherein REP is a repeating unit having the structure:

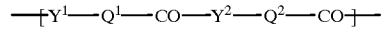

wherein $Y^1$ is O or $NR^3$ and $Y^2$ is O or $NR^4$ and one of $Q^1$ or $Q^2$ in a repeating unit is $-(CH_2)_w-$, where w is an integer ranging from 1 to 3 and the other of $Q^1$ or $Q^2$ in a repeating unit is $-CH(R')-$; and R', $R^3$ and $R^4$ can be H, a lower alkyl having from 1–3 carbon atoms, a non-cationic side group or a cationic side group with the proviso that there is one and only one cationic side group in each repeating unit.

30. A charge neutralized complex of claim 29 wherein said polycationic oligomer is $[Lys-Ala]_{28}$ and said nucleic acid is HN28ap or an analog or derivative thereof having 28 bases.

31. A pharmaceutical composition comprising a charge neutralized complex of claim 30 and a pharmaceutically-acceptable vehicle.

32. The pharmaceutical composition of claim 31 wherein said nucleic acid is an antisense, antigene or triplex-forming oligonucleotide.

33. The transfection composition of claim 1 wherein cationic side groups alternate with non-cationic side groups in the polycationic oligomer.

34. The transfection composition of claim 33 wherein the cationic side groups are selected from the group consisting of $-(CH_2)_4-NH_3^+$ or $-(CH_2)_3-NH-C(NH_2)=NH_2^+$.

35. The transfection composition of claim 1 wherein the repeating unit of the polycationic oligomer has the formula:

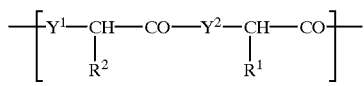

where one of $Y^1$ or $Y^2$ is O and the other of $Y^1$ or $Y^2$ is NH.

36. The transfection composition of claim 35 wherein in the polycationic oligomer r1 and r2 are 0.

37. The transfection composition of claim 36 wherein the cationic side group of the polycationic oligomer is $-(CH_2)_4-NH_3^+$ or $-(CH_2)_3-NH-C(NH_2)=NH_2^+$.

38. The transfection composition of claim 35 wherein the number of repeating units n in the polycationic oligomer is about 10 to about 100.

* * * * *

UNITED STATES PATENT AND TRADEMARK OFFICE
CERTIFICATE OF CORRECTION

PATENT NO. : 6,153,596
DATED : November 28, 2000
INVENTOR(S) : Liotta et al.

It is certified that error appears in the above-identified patent and that said Letters Patent is hereby corrected as shown below:

Title page,
Item [56], References Cited, OTHER PUBLICATIONS, in the "Zhou, X. et al." reference, please delete "(1990)" and replace with -- (1991) --.

Column 2,
Line 46, delete "ligonucleotide" and replace with -- oligonucleotide --.

Column 7,
Line 37, "WO91/19735" should be the start of a new paragraph.

Column 39,
Line 30, delete "2×10" and replace with -- $2\times10^5$ --.

Column 40,
Line 36, please add the following chemical schemes:
--

Scheme 1A

Fmoc-[Lys(tBoc)-Lac]$_n$-OBn

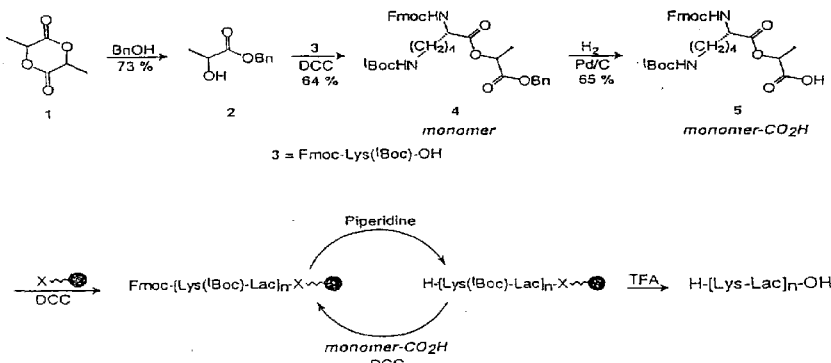

UNITED STATES PATENT AND TRADEMARK OFFICE
CERTIFICATE OF CORRECTION

PATENT NO.   : 6,153,596
DATED        : November 28, 2000
INVENTOR(S)  : Liotta et al.

It is certified that error appears in the above-identified patent and that said Letters Patent is hereby corrected as shown below:

Scheme 1B

Fmoc-[Lys(tBoc)-Lac]n-OBn

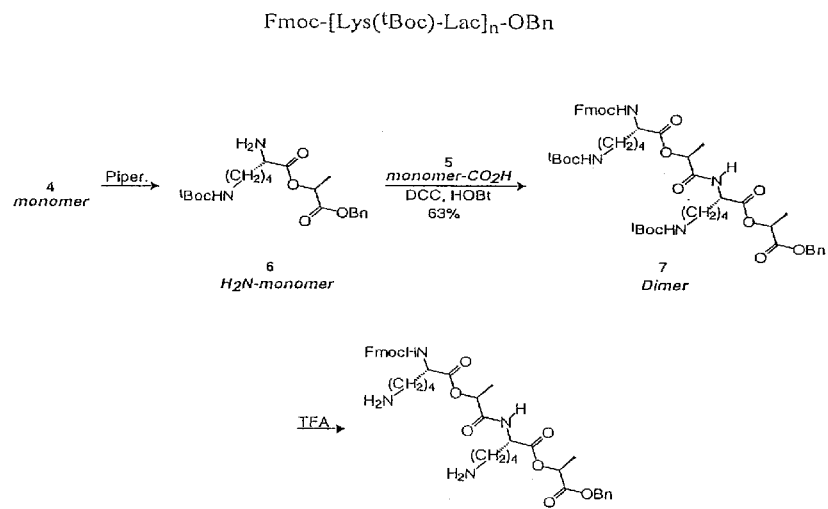

Scheme 3 tBoc-[Lys(Cbz)-Ala]n-OMe

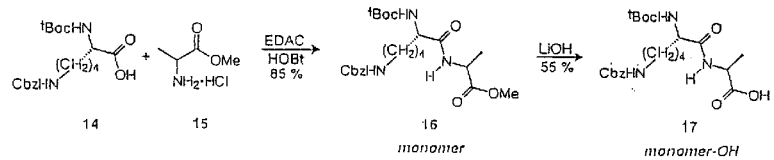

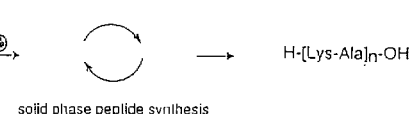

solid phase peptide synthesis

UNITED STATES PATENT AND TRADEMARK OFFICE
CERTIFICATE OF CORRECTION

PATENT NO. : 6,153,596  
DATED : November 28, 2000  
INVENTOR(S) : Liotta et al.

Page 3 of 6

It is certified that error appears in the above-identified patent and that said Letters Patent is hereby corrected as shown below:

Scheme 4

DHT Tether from Glutamic acid

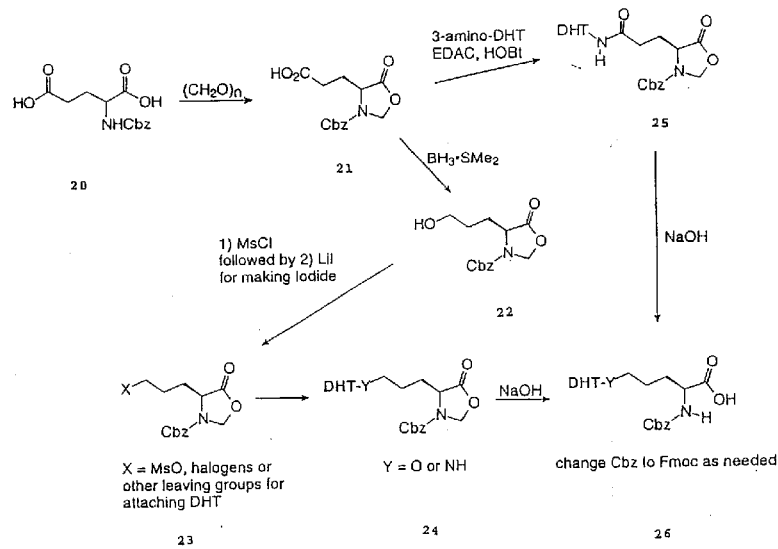

Scheme 5A

*DHT* Tether from Malic Acid (1)

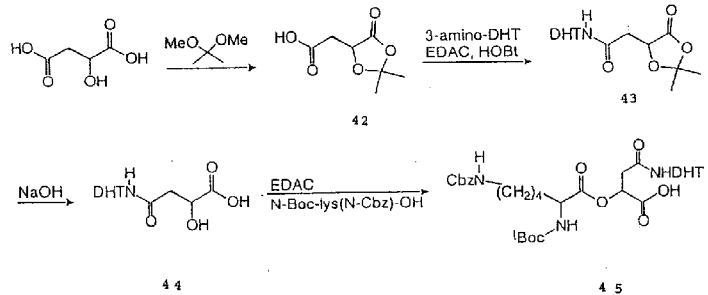

UNITED STATES PATENT AND TRADEMARK OFFICE
CERTIFICATE OF CORRECTION

PATENT NO.   : 6,153,596
DATED        : November 28, 2000
INVENTOR(S)  : Liotta et al.

It is certified that error appears in the above-identified patent and that said Letters Patent is hereby corrected as shown below:

Scheme 5B

*DHT* Tether from Malic Acid (2)

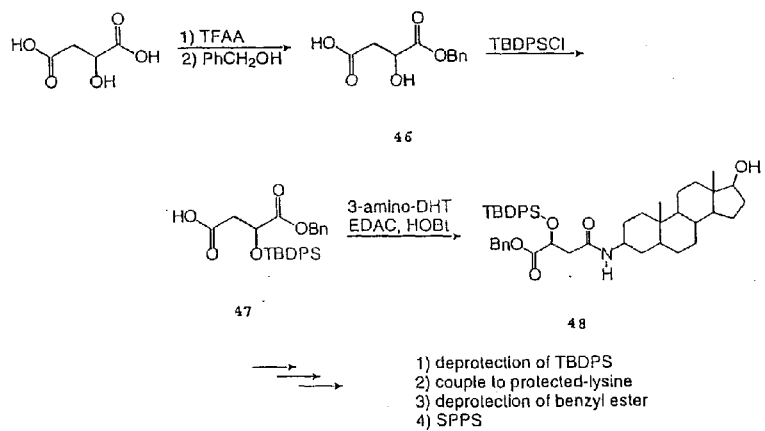

1) deprotection of TBDPS
2) couple to protected-lysine
3) deprotection of benzyl ester
4) SPPS Scheme 6     3-Amino(spacer)-DHT

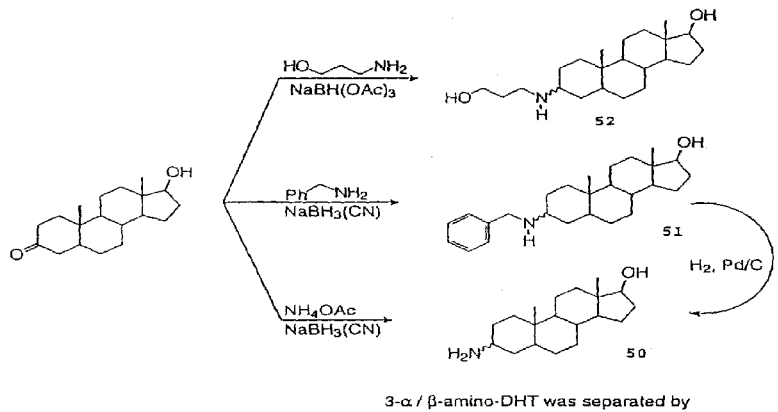

3-α / β-amino-DHT was separated by column chromatography or recrystalization

UNITED STATES PATENT AND TRADEMARK OFFICE
CERTIFICATE OF CORRECTION

PATENT NO. : 6,153,596
DATED : November 28, 2000
INVENTOR(S) : Liotta et al.

It is certified that error appears in the above-identified patent and that said Letters Patent is hereby corrected as shown below:

Scheme 7

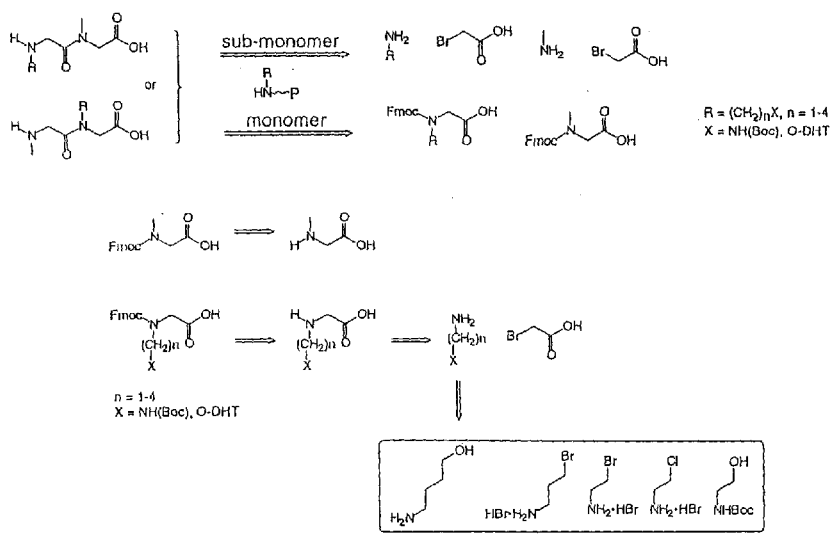

Please add the following chemical table:
--
Table 1: Exemplary Monomers

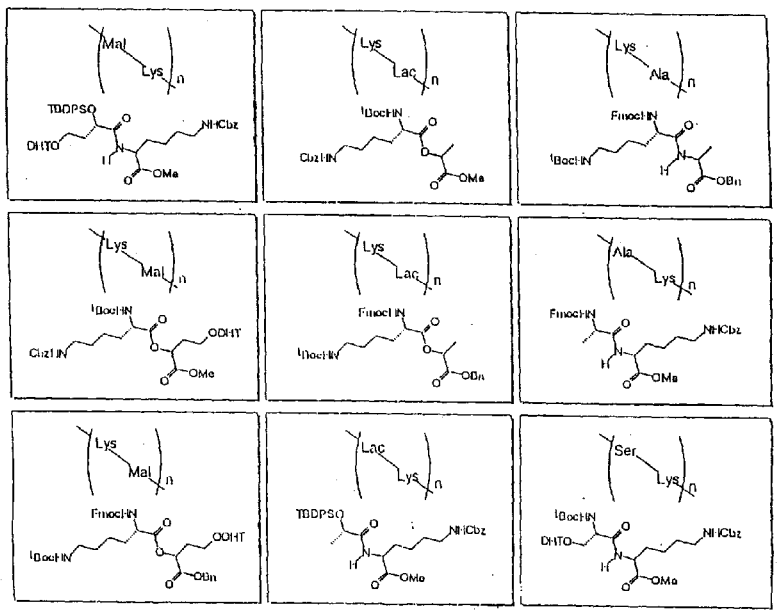

--

UNITED STATES PATENT AND TRADEMARK OFFICE
CERTIFICATE OF CORRECTION

PATENT NO.    : 6,153,596
DATED         : November 28, 2000
INVENTOR(S)   : Liotta et al.

It is certified that error appears in the above-identified patent and that said Letters Patent is hereby corrected as shown below:

Column 45,
Line 57, delete "or –CH$_2$)$_3$" and replace with -- or (–CH$_2$)$_3$ --.

Signed and Sealed this

Twentieth Day of May, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,153,596
DATED : November 28, 2000
INVENTOR(S) : Liotta et al.

It is certified that error appears in the above-identified patent and that said Letters Patent is hereby corrected as shown below:

Title page,
Item [56], References Cited, OTHER PUBLICATIONS, in the "Zhou, X. et al." reference, please delete "(1990)" and replace with -- (1991) --.

Column 2,
Line 46, delete "ligonucleotide" and replace with -- oligonucleotide --.

Column 7,
Line 37, "WO91/19735" should be the start of a new paragraph.

Column 39,
Line 30, delete "2×10" and replace with -- $2 \times 10^5$ --.

Column 40,
Line 36, please add the following chemical schemes:
--

Scheme 1A

Fmoc-[Lys(tBoc)-Lac]$_n$-OBn

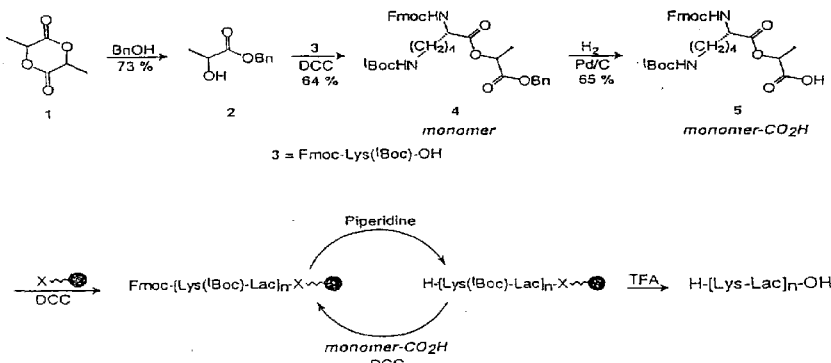

UNITED STATES PATENT AND TRADEMARK OFFICE
CERTIFICATE OF CORRECTION

PATENT NO.   : 6,153,596  
DATED        : November 28, 2000  
INVENTOR(S)  : Liotta et al.

Page 2 of 6

It is certified that error appears in the above-identified patent and that said Letters Patent is hereby corrected as shown below:

Scheme 1B

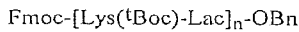

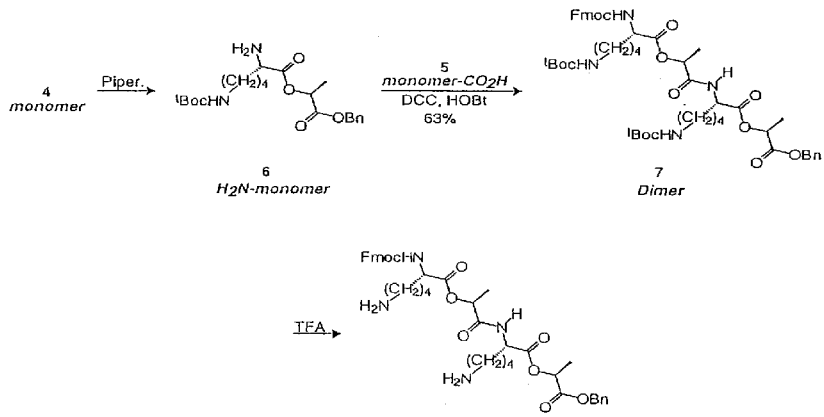

Scheme 3

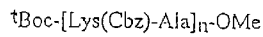

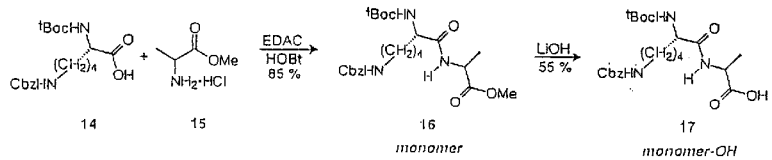

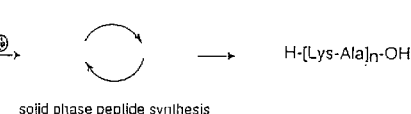

solid phase peptide synthesis

UNITED STATES PATENT AND TRADEMARK OFFICE
CERTIFICATE OF CORRECTION

PATENT NO. : 6,153,596
DATED : November 28, 2000
INVENTOR(S) : Liotta et al.

It is certified that error appears in the above-identified patent and that said Letters Patent is hereby corrected as shown below:

Scheme 2

TBDPS-[Lac-Lys(Cbz)]n-OMe

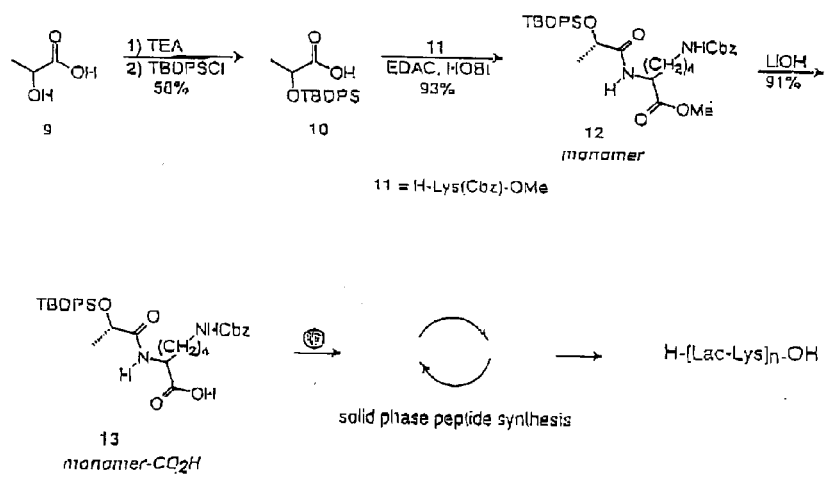

11 = H-Lys(Cbz)-OMe

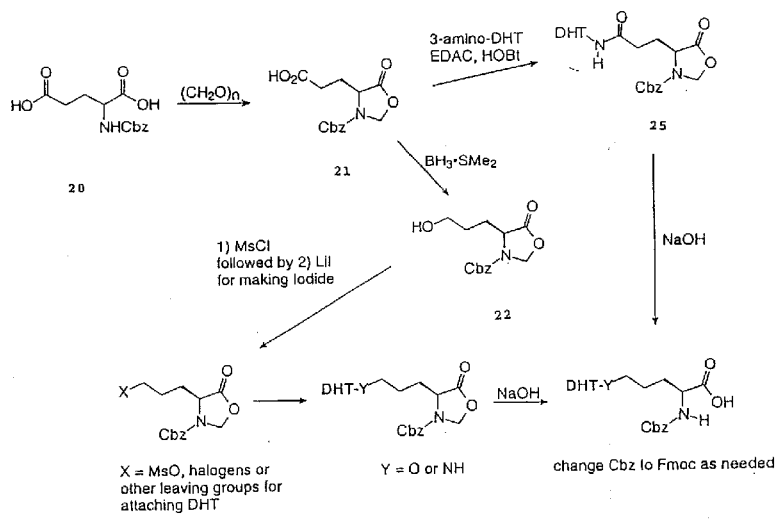

Scheme 4

DHT Tether from Glutamic acid

UNITED STATES PATENT AND TRADEMARK OFFICE
CERTIFICATE OF CORRECTION

PATENT NO.    : 6,153,596
DATED         : November 28, 2000
INVENTOR(S)   : Liotta et al.

Page 4 of 6

It is certified that error appears in the above-identified patent and that said Letters Patent is hereby corrected as shown below:

Scheme 5A

*DHT* Tether from Malic Acid (1)

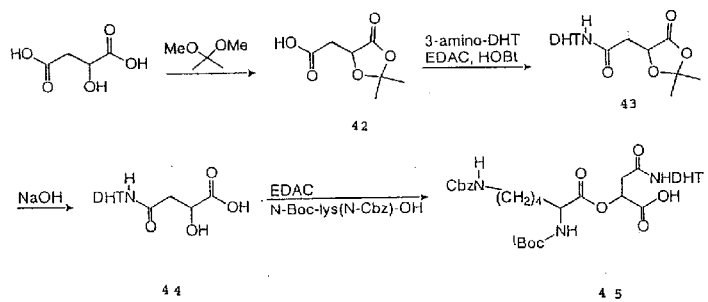

Scheme 5B

*DHT* Tether from Malic Acid (2)

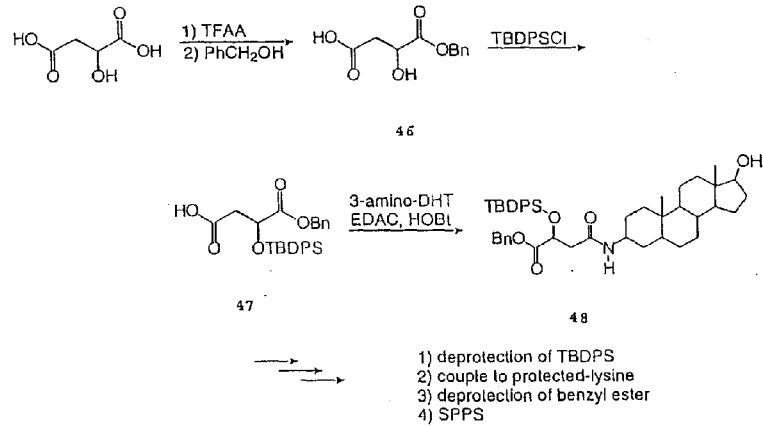

1) deprotection of TBDPS
2) couple to protected-lysine
3) deprotection of benzyl ester
4) SPPS

UNITED STATES PATENT AND TRADEMARK OFFICE
CERTIFICATE OF CORRECTION

PATENT NO. : 6,153,596
DATED : November 28, 2000
INVENTOR(S) : Liotta et al.

It is certified that error appears in the above-identified patent and that said Letters Patent is hereby corrected as shown below:

Scheme 6    3-Amino(spacer)-DHT

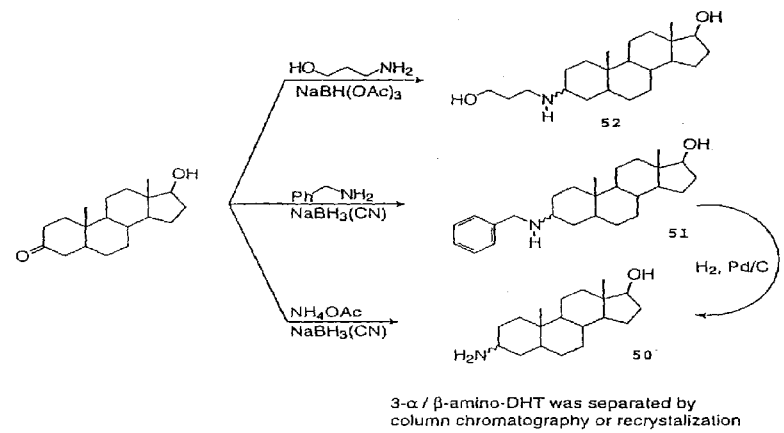

3-α / β-amino-DHT was separated by column chromatography or recrystalization

Scheme 7

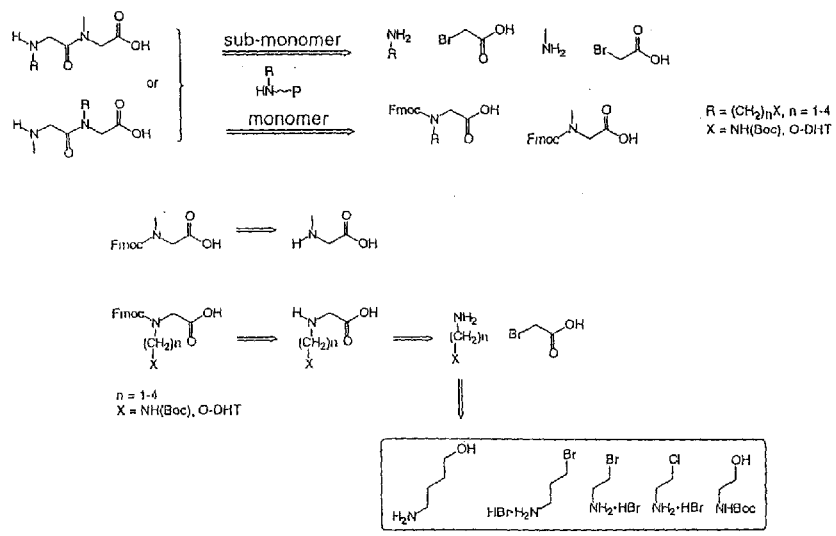

UNITED STATES PATENT AND TRADEMARK OFFICE
CERTIFICATE OF CORRECTION

PATENT NO. : 6,153,596
DATED : November 28, 2000
INVENTOR(S) : Liotta et al.

It is certified that error appears in the above-identified patent and that said Letters Patent is hereby corrected as shown below:

Please add the following chemical table:
--

Table 1: Exemplary Monomers

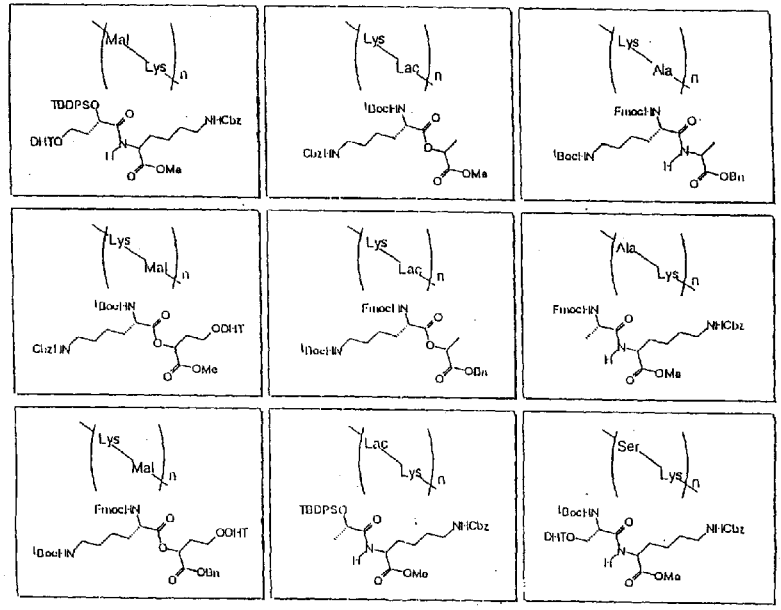

--

Column 45,
Line 57, delete "or $-CH_2)_3$" and replace with -- or $(-CH_2)_3$ --.

This certificate supersedes Certificate of Correction issued May 20, 2003.

Signed and Sealed this

Eighth Day of July, 2003

JAMES E. ROGAN
*Director of the United States Patent and Trademark Office*